(12) United States Patent
Kobunai et al.

(10) Patent No.: US 8,440,398 B2
(45) Date of Patent: May 14, 2013

(54) METHOD FOR PREDICTION OF SENSITIVITY TO 5-FLUOROURACIL-TYPE ANTICANCER AGENT

(75) Inventors: Takashi Kobunai, Tokushima (JP); Akio Ooyama, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 278 days.

(21) Appl. No.: 12/161,957

(22) PCT Filed: Jan. 23, 2007

(86) PCT No.: PCT/JP2007/050933
§ 371 (c)(1),
(2), (4) Date: Jul. 23, 2008

(87) PCT Pub. No.: WO2007/086351
PCT Pub. Date: Aug. 2, 2007

(65) Prior Publication Data
US 2009/0197264 A1 Aug. 6, 2009

(30) Foreign Application Priority Data
Jan. 25, 2006 (JP) .................................. 2006-016367

(51) Int. Cl.
*C12Q 1/68* (2006.01)
(52) U.S. Cl.
USPC .......................................................... 435/6.1
(58) Field of Classification Search .................... None
See application file for complete search history.

(56) References Cited

U.S. PATENT DOCUMENTS

2002/0123620 A1 9/2002 Danenberg
2003/0165840 A1* 9/2003 Danenberg ...................... 435/6

FOREIGN PATENT DOCUMENTS

WO WO97/35034 A1 9/1997

OTHER PUBLICATIONS

International Search Report for PCT/JP2007/050933 mailed May 15, 2007.
A. Beck et al., A Role for Dihydropyrimidine Dehydrogenase and Thymidylate Synthase in Tumour Sensitivity to Fluorouracil, European Journal of Cancer (1994) vol. 30, Issue 10, pp. 1517-1522.
Akio Oyama et al., "Hito Shuokabu no Morateki idenshi Hatsugen Kaiseki ni yoru Yakuzai Kanjusei Kitei Inshi Koho no Tansaku", Dai 26 Kai Annual Meeting of the Molecular Biology Socienty of Japan Program Koen Yoshishu, Nov. 25, 2003, p. 907,3PC-111.
S.J. Freemantle, et al. Molecular Characterisation of two cell lines selected for resistance to the folate-based thymidylate synthase inhibitor, ZD1694, Br. J. Cancer, May 1995; 71 (5): 925-30.
McLeod HL et al., Variation in Topoisomerase I gene copy number as a mechanism for intrinsic drug sensitivity. Br J. Cancerl, Aug. 1996; 74 (4): 508-12.
Bussey KJ et al., Integrating data on DNA copy number with gene expression levels and drug sensitivities with the NCI-60 cell line panel., Mol. Cancer Ther. Apr. 2006; 5 (4): 853-67.
Bussey, KJ et al., Correlating gene expression and drug sensitivity with DNA copy number in the NC160 panel of human cancer cell lines., Proceedings of the American Association for Cancer Research, 2003, vol. 44, $2^{nd}$ ed., p. 211, #1046.
Garraway, Levi A. et al., "Integrative Genomic Analyses Identify MITF as a Lineage Survival Oncogene Amplified in Malignant Melanoma," Nature, vol. 436, pp. 117-122, Jul. 7, 2005.
Lu, Zhihong et al., "Dihydopyrimidine Dehydrogenase Activity in Human Peripheral Blood Mononuclear cells and Liver: Population Characteristics, Newly Identified deficient Patients, and Clinical Implication in 5-Fluorouracil Chemotherapy," Cancer research, pp. 5433-5438, Nov. 15, 1993.
English translation of the International Preliminary Report on Patentability for PCT/JP2007/050933 mailed Aug. 7, 2008.
Svetlana A. Shestopal et al., "Molecular cloning and characterization of the human dihydropyrimidine dehydrogenase promoter," Biochimica et Biophysica Acta gene structure and expression, 2000, vol. 1494, Issues 1-2, p. 162-169.
Hiroshi Yokota et al., "cDNA Cloning and Chromosome Mapping of Human Dihydropyrimidine Dehydrogenase, an Enzyme Associated with 5-Fluorouracil Toxicity and Congenital Thymine Uraciluria," The Journal of Biological Chemistry, 1994, vol. 269, No. 37, p. 23192-23196.

* cited by examiner

*Primary Examiner* — Christopher M. Babic
(74) *Attorney, Agent, or Firm* — DLA Piper (US)

(57) ABSTRACT

A factor affecting sensitivities to anticancer agents is analyzed and the validity of the factor is demonstrated.

The present invention provides a method for predicting sensitivities to 5-fluorouracil-based anticancer agents using the copy number of dihydropyrimidine dehydrogenase gene as an indicator. Also disclosed are a kit and primers for use in predicting sensitivities to 5-fluorouracil-based anticancer agents.

5 Claims, 8 Drawing Sheets

SEQUENCE LISTING

<160> NUMBER OF SEQ ID NOS: 17

<210> SEQ ID NO 1
<211> LENGTH: 4407
<212> TYPE: DNA
<213> ORGANISM: Homo sapiens

<400> SEQUENCE: 1

| | | | | | | |
|---|---|---|---|---|---|---|
| tttcgactcg | cgctccggct | gctgtcactt | ggctctctgg | ctggagcttg | aggacgcaag | 60 |
| gagggtttgt | cactggcaga | ctcgagactg | taggcactgc | catggcccct | gtgctcagta | 120 |
| aggactcggc | ggacatcgag | agtatcctgg | ctttaaatcc | tcgaacacaa | actcatgcaa | 180 |
| ctctgtgttc | cacttcggcc | aagaaattag | acaagaaaca | ttggaaaaga | aatcctgata | 240 |
| agaactgctt | taattgtgag | aagctggaga | ataattttga | tgacatcaag | cacacgactc | 300 |
| ttggtgagcg | aggagctctc | cgagaagcaa | tgagatgcct | gaaatgtgca | gatgccccgt | 360 |
| gtcagaagag | ctgtccaact | aatcttgata | ttaaatcatt | catcacaagt | attgcaaaca | 420 |
| agaactatta | tggagctgct | aagatgatat | tttctgacaa | cccacttggt | ctgacttgtg | 480 |
| gaatggtatg | tccaacctct | gatctatgtg | taggtggatg | caatttatat | gccactgaag | 540 |
| agggacccat | taatattggt | ggattgcagc | aatttgctac | tgaggtattc | aaagcaatga | 600 |
| gtatcccaca | gatcagaaat | ccttcgctgc | ctcccccaga | aaaaatgtct | gaagcctatt | 660 |
| ctgcaaagat | tgctcttttt | ggtgctgggc | ctgcaagtat | aagttgtgct | tcctttttgg | 720 |
| ctcgattggg | gtactctgac | atcactatat | ttgaaaaaca | agaatatgtt | ggtggtttaa | 780 |
| gtacttctga | aattcctcag | ttccggctgc | cgtatgatgt | agtgaatttt | gagattgagc | 840 |
| taatgaagga | ccttggtgta | agataatttt | gcggtaaaag | cctttcagtg | aatgaaatga | 900 |
| ctcttagcac | tttgaaagaa | aaaggctaca | agctgctttt | cattggaata | ggtttgccag | 960 |
| aacccaataa | agatgccatc | ttccaaggcc | tgacgcagga | ccaggggttt | tatacatcca | 1020 |
| aagactttt | gccacttgta | gccaaaggca | gtaaagcagg | aatgtgcgcc | tgtcactctc | 1080 |
| cattgccatc | gatacgggga | gtcgtgattg | tacttggagc | tggagacact | gccttcgact | 1140 |
| gtgcaacatc | tgctctacgt | tgtggagctc | gccgagtgtt | catcgtcttc | agaaaaggct | 1200 |
| ttgttaatat | aagagctgtc | cctgaggaga | tggagcttgc | taaggaagaa | aagtgtgaat | 1260 |
| ttctgccatt | cctgtcccca | cggaaggtta | tagtaaaagg | tgggagaatt | gttgctatgc | 1320 |
| agtttgttcg | gacagagcaa | gatgaaactg | gaaaatggaa | tgaagatgaa | gatcagatgg | 1380 |
| tccatctgaa | agccgatgtg | gtcatcagtg | cctttggttc | agttctgagt | gatcctaaag | 1440 |
| taaagaagc | cttgagcccct | ataaaattta | acagatgggg | tctcccagaa | gtagatccag | 1500 |
| aaactatgca | aactagtgaa | gcatgggtat | ttgcaggtgg | tgatgtcgtt | ggtttggcta | 1560 |
| acactacagt | ggaatcggtg | aatgatggaa | agcaagcttc | ttggtacatt | cacaaatacg | 1620 |
| tacagtcaca | atatggagct | tccgtttctg | ccaagcctga | actaccctc | ttttacactc | 1680 |
| ctattgatct | ggtggacatt | agtgtagaaa | tggccggatt | gaagtttata | aatccttttg | 1740 |
| gtcttgctag | cgcaactcca | gccaccagca | catcaatgat | tcgaagagct | tttgaagctg | 1800 |
| gatgggggttt | tgccctcacc | aaaacttttct | ctcttgataa | ggacattgtg | acaaatgttt | 1860 |
| cccccagaat | catccgggga | accacctctg | gccccatgta | tggccctgga | caaagctcct | 1920 |
| ttctgaatat | tgagctcatc | agtgagaaaa | cggctgcata | ttggtgtcaa | agtgtcactg | 1980 |
| aactaaaggc | tgacttccca | gacaacattg | tgattgctag | cattatgtgc | agttacaata | 2040 |

```
aaaatgactg acggaactt gccaagaagt ctgaggattc tggagcagat gccctggagt   2100
taaatttatc atgtccacat ggcatgggag aaagaggaat gggcctggcc tgtgggcagg   2160
atccagagct ggtgcggaac atctgccgct gggttaggca agctgttcag attcctttt   2220 ttgccaagct gaccccaaat gtcactgata ttgtgagcat cgcaagagct gcaaaggaag   2280
gtggtgccaa tggcgttaca gccaccaaca ctgtctcagg tctgatggga ttaaaatctg   2340
atggcacacc ttggccagca gtggggattg caaagcgaac tacatatgga ggagtgtctg   2400
ggacagcaat cagacctatt gctttgagag ctgtgacctc cattgctcgt gctctgcctg   2460
gatttcccat tttggctact ggtggaattg actctgctga agtggtcttc agtttctcc   2520 atagtggtgc ttccgtcctc caggtatgca gtgccattca gaatcaggat ttcactgtga   2580
tcgaagacta ctgcactggc ctcaaagccc tgctttatct gaaaagcatt gaagaactac   2640
aagactggga tggacagagt ccagctactg tgagtcacca gaaagggaaa ccagttccac   2700
gtatagctga actcatggac aagaaactgc caagttttgg accttatctg gaacagcgca   2760
agaaaatcat agcagaaaac aagattagac tgaaagaaca aaatgtagct ttttcaccac   2820
ttaagagaag ctgtttttatc cccaaaaggc ctattcctac catcaaggat gtaataggaa   2880
aagcactgca gtaccttgga acatttggtg aattgagcaa cgtagagcaa gttgtggcta   2940
tgattgatga agaaatgtgt atcaactgtg gtaaatgcta catgacctgt aatgattctg   3000
gctaccaggc tatacagttt gatccagaaa cccacctgcc caccataacc gacacttgta   3060
caggctgtac tctgtgtctc agtgtttgcc ctattgtcga ctgcatcaaa atggtttcca   3120
ggacaacacc ttatgaacca agagaggcg taccttatc tgtgaatccg gtgtgttaag   3180
gtgatttgtg aaacagttgc tgtgaacttt catgtcacct acatatgctg atctcttaaa   3240
atcatgatcc ttgtgttcag ctcttttccaa attaaaacaa atatacattt tctaaataaa   3300
aatatgtaat ttcaaaatac atttgtaagt gtaaaaaatg tctcatgtca atgaccattc   3360
aattagtggc ataaaataga ataattcttt tctgaggata gtagttaaat aactgtgtgg   3420
cagttaattg gatgttcact gccagttgtc ttatgtgaaa aattaacttt ttgtgtggca   3480
attagtgtga cagtttccaa attgccctat gctgtgctcc atatttgatt tctaattgta   3540
agtgaaatta agcattttga acaaagtac tctttaacat acaagaaaat gtatccaagg   3600
aaacatttta tcaataaaaa ttacctttaa ttttaatgct gtttctaaga aaatgtagtt   3660
agctccataa agtacaaatg aagaaagtca aaattatttt gctatggcag gataagaaag   3720
cctaaaattg agtttgtgga ctttattaag taaaatcccc ttcgctgaaa ttgcttattt   3780
ttggtgttgg atagaggata gggagaatat ttactaacta aataccattc actactcatg   3840
cgtgagatgg gtgtacaaac tcatcctctt ttaatggcat ttctctttaa actatgttcc   3900
taaccaaatg agatgatagg atagatcctg gttaccactc ttttactgtg cacatatggg   3960
ccccggaatt ctttaatagt caccttcatg attatagcaa ctaatgtttg aacaaagctc   4020
aaagtatgca atgcttcatt attcaagaat gaaaaatata atgttgataa tatatattaa   4080
gtgtgccaaa tcagtttgac tactctctgt tttagtgttt atgtttaaaa gaatatatt   4140 ttttgttatt attagataat attttttgtat ttctctattt tcataatcag taaatagtgt   4200
catataaact catttatctc ctcttcatgg catcttcaat atgaatctat aagtagtaaa   4260
tcagaaagta acaatctatg gcttatttct atgacaaatt caagagctag aaaaataaaa   4320
tgtttcatta tgcactttta gaaatgcata tttgccacaa aacctgtatt actgaataat   4380
atcaaataaa atatcataaa gcattt                                        4407
```

```
<210> SEQ ID NO 2
<211> LENGTH: 1025
<212> TYPE: PRT
<213> ORGANISM: Homo sapiens

<400> SEQUENCE: 2

Met Ala Pro Val Leu Ser Lys Asp Ser Ala Asp Ile Glu Ser Ile Leu
1               5                   10                  15

Ala Leu Asn Pro Arg Thr Gln Thr His Ala Thr Leu Cys Ser Thr Ser
            20                  25                  30

Ala Lys Lys Leu Asp Lys Lys His Trp Lys Arg Asn Pro Asp Lys Asn
        35                  40                  45

Cys Phe Asn Cys Glu Lys Leu Glu Asn Asn Phe Asp Asp Ile Lys His
    50                  55                  60

Thr Thr Leu Gly Glu Arg Gly Ala Leu Arg Glu Ala Met Arg Cys Leu
65                  70                  75                  80

Lys Cys Ala Asp Ala Pro Cys Gln Lys Ser Cys Pro Thr Asn Leu Asp
                85                  90                  95

Ile Lys Ser Phe Ile Thr Ser Ile Ala Asn Lys Asn Tyr Tyr Gly Ala
            100                 105                 110

Ala Lys Met Ile Phe Ser Asp Asn Pro Leu Gly Leu Thr Cys Gly Met
        115                 120                 125

Val Cys Pro Thr Ser Asp Leu Cys Val Gly Gly Cys Asn Leu Tyr Ala
    130                 135                 140

Thr Glu Glu Gly Pro Ile Asn Ile Gly Gly Leu Gln Gln Phe Ala Thr
145                 150                 155                 160

Glu Val Phe Lys Ala Met Ser Ile Pro Gln Ile Arg Asn Pro Ser Leu
                165                 170                 175

Pro Pro Pro Glu Lys Met Ser Glu Ala Tyr Ser Ala Lys Ile Ala Leu
            180                 185                 190

Phe Gly Ala Gly Pro Ala Ser Ile Ser Cys Ala Ser Phe Leu Ala Arg
        195                 200                 205

Leu Gly Tyr Ser Asp Ile Thr Ile Phe Glu Lys Gln Glu Tyr Val Gly
    210                 215                 220

Gly Leu Ser Thr Ser Glu Ile Pro Gln Phe Arg Leu Pro Tyr Asp Val
225                 230                 235                 240

Val Asn Phe Glu Ile Glu Leu Met Lys Asp Leu Gly Val Lys Ile Ile
                245                 250                 255

Cys Gly Lys Ser Leu Ser Val Asn Glu Met Thr Leu Ser Thr Leu Lys
            260                 265                 270

Glu Lys Gly Tyr Lys Ala Ala Phe Ile Gly Ile Gly Leu Pro Glu Pro
        275                 280                 285

Asn Lys Asp Ala Ile Phe Gln Gly Leu Thr Gln Asp Gln Gly Phe Tyr
    290                 295                 300

Thr Ser Lys Asp Phe Leu Pro Leu Val Ala Lys Gly Ser Lys Ala Gly
305                 310                 315                 320

Met Cys Ala Cys His Ser Pro Leu Pro Ser Ile Arg Gly Val Val Ile
                325                 330                 335

Val Leu Gly Ala Gly Asp Thr Ala Phe Asp Cys Ala Thr Ser Ala Leu
            340                 345                 350

Arg Cys Gly Ala Arg Arg Val Phe Ile Val Phe Arg Lys Gly Phe Val
        355                 360                 365

Asn Ile Arg Ala Val Pro Glu Glu Met Glu Leu Ala Lys Glu Glu Lys
    370                 375                 380
```

-continued

```
Cys Glu Phe Leu Pro Phe Leu Ser Pro Arg Lys Val Ile Val Lys Gly
385                 390                 395                 400

Gly Arg Ile Val Ala Met Gln Phe Val Arg Thr Glu Gln Asp Glu Thr
            405                 410                 415

Gly Lys Trp Asn Glu Asp Glu Asp Gln Met Val His Leu Lys Ala Asp
                420                 425                 430

Val Val Ile Ser Ala Phe Gly Ser Val Leu Ser Asp Pro Lys Val Lys
            435                 440                 445

Glu Ala Leu Ser Pro Ile Lys Phe Asn Arg Trp Gly Leu Pro Glu Val
        450                 455                 460

Asp Pro Glu Thr Met Gln Thr Ser Glu Ala Trp Val Phe Ala Gly Gly
465                 470                 475                 480

Asp Val Val Gly Leu Ala Asn Thr Thr Val Glu Ser Val Asn Asp Gly
                485                 490                 495

Lys Gln Ala Ser Trp Tyr Ile His Lys Tyr Val Gln Ser Gln Tyr Gly
            500                 505                 510

Ala Ser Val Ser Ala Lys Pro Glu Leu Pro Leu Phe Tyr Thr Pro Ile
        515                 520                 525

Asp Leu Val Asp Ile Ser Val Glu Met Ala Gly Leu Lys Phe Ile Asn
530                 535                 540

Pro Phe Gly Leu Ala Ser Ala Thr Pro Ala Thr Ser Thr Ser Met Ile
545                 550                 555                 560

Arg Arg Ala Phe Glu Ala Gly Trp Gly Phe Ala Leu Thr Lys Thr Phe
                565                 570                 575

Ser Leu Asp Lys Asp Ile Val Thr Asn Val Ser Pro Arg Ile Ile Arg
            580                 585                 590

Gly Thr Thr Ser Gly Pro Met Tyr Gly Pro Gly Gln Ser Ser Phe Leu
        595                 600                 605

Asn Ile Glu Leu Ile Ser Glu Lys Thr Ala Ala Tyr Trp Cys Gln Ser
610                 615                 620

Val Thr Glu Leu Lys Ala Asp Phe Pro Asp Asn Ile Val Ile Ala Ser
625                 630                 635                 640

Ile Met Cys Ser Tyr Asn Lys Asn Asp Trp Thr Glu Leu Ala Lys Lys
                645                 650                 655

Ser Glu Asp Ser Gly Ala Asp Ala Leu Glu Leu Asn Leu Ser Cys Pro
            660                 665                 670

His Gly Met Gly Glu Arg Gly Met Gly Leu Ala Cys Gly Gln Asp Pro
        675                 680                 685

Glu Leu Val Arg Asn Ile Cys Arg Trp Val Arg Gln Ala Val Gln Ile
690                 695                 700

Pro Phe Phe Ala Lys Leu Thr Pro Asn Val Thr Asp Ile Val Ser Ile
705                 710                 715                 720

Ala Arg Ala Ala Lys Glu Gly Gly Ala Asn Gly Val Thr Ala Thr Asn
                725                 730                 735

Thr Val Ser Gly Leu Met Gly Leu Lys Ser Asp Gly Thr Pro Trp Pro
            740                 745                 750

Ala Val Gly Ile Ala Lys Arg Thr Thr Tyr Gly Gly Val Ser Gly Thr
        755                 760                 765

Ala Ile Arg Pro Ile Ala Leu Arg Ala Val Thr Ser Ile Ala Arg Ala
770                 775                 780

Leu Pro Gly Phe Pro Ile Leu Ala Thr Gly Gly Ile Asp Ser Ala Glu
785                 790                 795                 800

Ser Gly Leu Gln Phe Leu His Ser Gly Ala Ser Val Leu Gln Val Cys
                805                 810                 815
```

Ser Ala Ile Gln Asn Gln Asp Phe Thr Val Ile Glu Asp Tyr Cys Thr
                820                 825                 830

Gly Leu Lys Ala Leu Leu Tyr Leu Lys Ser Ile Glu Glu Leu Gln Asp
            835                 840                 845

Trp Asp Gly Gln Ser Pro Ala Thr Val Ser His Gln Lys Gly Lys Pro
850                 855                 860

Val Pro Arg Ile Ala Glu Leu Met Asp Lys Lys Leu Pro Ser Phe Gly
865                 870                 875                 880

Pro Tyr Leu Glu Gln Arg Lys Lys Ile Ala Glu Asn Lys Ile Arg
                885                 890                 895

Leu Lys Glu Gln Asn Val Ala Phe Ser Pro Leu Lys Arg Ser Cys Phe
            900                 905                 910

Ile Pro Lys Arg Pro Ile Pro Thr Ile Lys Asp Val Ile Gly Lys Ala
            915                 920                 925

Leu Gln Tyr Leu Gly Thr Phe Gly Glu Leu Ser Asn Val Glu Gln Val
            930                 935                 940

Val Ala Met Ile Asp Glu Met Cys Ile Asn Cys Gly Lys Cys Tyr
945                 950                 955                 960

Met Thr Cys Asn Asp Ser Gly Tyr Gln Ala Ile Gln Phe Asp Pro Glu
                965                 970                 975

Thr His Leu Pro Thr Ile Thr Asp Thr Cys Thr Gly Cys Thr Leu Cys
                980                 985                 990

Leu Ser Val Cys Pro Ile Val Asp Cys Ile Lys Met Val Ser Arg Thr
            995                 1000                1005

Thr Pro Tyr Glu Pro Lys Arg Gly Val Pro Leu Ser Val Asn Pro
    1010                1015                1020

Val Cys
    1025

<210> SEQ ID NO 3
<211> LENGTH: 4452
<212> TYPE: DNA
<213> ORGANISM: Mus musculus

<400> SEQUENCE: 3
ccacgcgtcc gggcaagctg aggctttggt gcggggctgg aggctgctgc agcagaggga     60
gggtctgtgt gcgggagtct gaggccagaa agcgctgcca tggcgggtgt gctgagcagg    120
gacgcgccgg acatcgagag tatcctggct ttaaaccctc gagtacaagc tcatgcaact    180
ctgcgttcca ccgcagccaa gaaactagac aagaaacact ggaaaaggaa cacggacaag    240
aactgcttta cctgtgagaa gctggagagt aattttgatg acatcaagca cacgactctt    300
ggtgagcgag gagctctccg agaagcagtg agatgcctga gtgcgcaga tgctccctgc    360 cagaagagct gtcccacatc tcttgacatt aaatcattta tcacaagtat cgccaacaag    420
aactactatg gtgcagctaa gctgattttt tctgataacc tcttggtct tacttgtgga    480 atggtttgtc caacatctga cctctgtgtt ggaggatgca acttacatgc tgctgaagag    540
ggaccaatta atattggtgg gctgcagcag tttgctactg aggtgttcaa agcaatgaac    600
atcccacaga tcagaaaccc atcgctgcct cctccggaac atatgccgga agcctactca    660
gcaaaaattg cacttttggg tgcagggcct gcgagtataa gctgtgcctc cttttttggct    720 cggttgggct attccaacat tactatattc gaaaaacaag aatatgttgg tggtttaagc    780
acttctgaaa tccctcagtt tcgactccca tatgacgtcg tgaattttga gattgagctc    840
atgaaggacc ttggtgtaaa gataatttgt ggtaaaagcc tttccaccga tgaaatgact    900

```
cttagctctt tgaaagaaaa tggctacaga gctgcattta ttggaatagg cttgccagaa      960
cccaaaaagg accatatttt ccaaggcttg acacaagtcc agggatttta cacatctaaa     1020
gactttctgc cacttgtcgc aaaagcagt aaaacaggaa tgtgcgcctg tcactctcca     1080
ttgccatcca taagggagc cgtgattgta ctcggagctg agatactgc gtttgactgt     1140 gcaacatccg ctctgcgctg tggagccctt cgcgtgttca tcgtcttcag aaagggcttt     1200
gttaatattc gagctgttcc agaggagatg gagctcgcta aggaagagaa atgtgaattt     1260 ttgccttttcc tctcgccacg gaaggttata gtcaaagatg gaaagattgt ggcaatgcaa     1320
tttgttcgaa ctgagcaaga tgaaaccgga aactgggtgg aagatgaaga gcagacggtg     1380
cggctaaagg ctgatgtggt tattagtgcc tttggatctg tcctggagga tcccaaagtg     1440
aaagaagcat tgagtcccat caagtttaac agatggggtc tcccagaagt aaatccagaa     1500
accatgcaaa ccagtgaacc atgggtgttt gcaggtggtg atgttgtggg tatggctaac     1560
accacagtgg aatctgtcaa cgatggaaag caagcttcat ggtacattca aagcacata     1620 caggcacaat atggaacctc agtgccttct cagcctacaa tgcccctatt ttacactccg     1680
gttgacttag tggacatcag cgtggaaatg gcagggttga ggtttcccaa tcccttggc     1740 cttgccagtg cgacaccagc cactagcaca ccaatgattc gaagggcctt tgaagctggc     1800
tggggttttg tctctgaccaa aactttctct cttgataagg acatcgtgac aaacgtctca     1860
ccaagaatca tccgggggac aacttctggc cccttgtatg gccctggaca aagctccttt     1920
cttaacattg agctcatcag tgagaaaaca gctgcatatt ggtgtcacag tgtcaccgaa     1980
ctaaaggctg acttcccgga caatatcctg atcgccagca tcatgtgcag ttacaacaag     2040
agtgactgga tggaactctc caaaatggct gaggcttctg gagcagatgc cctggagtta     2100
aatttatcgt gtccacatgg catggggag agaggaatgg gcctggcttg tgggcaggat     2160
ccagagctgt gaggaacat ctgtcgctgg gttaggcaag ctgttcgggt tccattttt     2220 gccaagttga ccccaaatgt cactgatatt gtaagcatcg caagagcagc aaaggaaggt     2280
ggagcagatg gtgtaacagc caccaacacc gtctcgggtc tgatgggact gaaagctgat     2340
ggcacaccct ggcctgctgt gggcattgga aggaggacta catatggagg agtgtcagga     2400
actgctatca ggcccattgc tttgagagct gtgaccgcca ttgcccgtgc tttgcctggg     2460
tttcctattt tggccacagg tggaattgac tcagctgaaa gtggacttca gtttcttcat     2520
agtggtgctt cagttcttca ggtatgcagc gctattcaga atcaggactt cactgtgatt     2580
gaagattact gcactggact caaagccctg ctttatctga gagcattga agagttagca     2640 gactgggatg gtcagagtcc acccattata agtcatcaga aagggaaacc agttccacgc     2700
gttgctgagc tcatgggaca gaaactgccc agctttggac cttaccttga acagcgcaag     2760
aaaatcatag cagcaagcaa aatcagacag aaagatcaaa acacagcttg ctcacctctc     2820
cagagaaagc actttaactc gcaaaagcct attcctgcca tcaaggatgt aattggaaaa     2880
tcactgcaat acctgggaac atttggtgag atgagcatca tggaacaagt tgtggccctg     2940
atcgatgagg aaatgtgcat caattgcggc aaatgttaca tgacctgtaa tgactctggc     3000
taccaggcta tccagttcga tccagaaact cacctgccta ccgttagcga cacatgtaca     3060
ggctgtactc tctgcctcag cgtctgccct attatggact gtatcaggat ggtttccagg     3120
gcaacacctt atcaaccaaa gagaggccta ccattagccg tgaagccggt gtgttaaggt     3180
gatttgtaag acagctgctg tgaactttga tattacccat gtaggctgat ctttaagaac     3240
aataacaatt gtaatcatta tgatcagttc tttccaaatt ttatagctga acaataacaa     3300
```

-continued

```
ttgtaatcat tatgatcagt tctttccaaa ttttatagct atgcatatat aatttctaaa    3360
taagtgtcta aattggaaaa caatgtctaa tgccagtgac aaattaatgg tcataaaatg    3420
gaataactct tctctgaggt agctggtgag taactgcaga ccagttaatt ggatgtgctc    3480
tgtccgttgt gtgctgtgaa aaattaactt tttcatggca attagcgtga caatttctaa    3540
attgccctat gccgtactca ctctttgatt tctaattgta aacgaaatga actattttgg    3600
aacggagtgc actttcatat acaggaaacc gtttccaagg aaacgctttg taattaaaaa    3660
ttacctgtaa ttttaacact gtttctaagg acatgtaatt agttccatta agaacaattg    3720
aagaaagtca aggcattatt tactatgaca aggggggaaga aaacctggaa gagggtttct    3780
agagttttct aaagtccccc tttgctgaag taactcactc ttcggtgctg gacacggaaa    3840
gggagattat ttcctgacta aaatgctgtt gaccacctga acaggtgtc agactgacca     3900 gggatggagt cctggccatt tttatttgaa taccaaagcg gtgttcctaa tgaaataaga    3960
tatcgaggtg aatgtctggt gaatggccca ctttcactga gcacagacag ctagatctgc    4020
ttcttttagt caccttcatt atgagagcaa ttaatgttca acaagggct agattacaca     4080 gcgctgagcc ataggcttca agattcaaca acaaagtgtg tcatatctga acctgctaca    4140 taataaaccct aactaacttt actttgatac tcatgtgaat tcaaaattaa tgaaagagaa   4200
atgtgtatct ttggatattg atcagtgttt ttccccatat cttattttt ataatcagta     4260 aatagcatca cataaattca tttattcctt ctttatggca cattttaaaa tgaatctata    4320
gaaagtaagt gagaaatgac aacctgtgga atatttctat gataaatgca agatatctac    4380
aagtgcattt taaaaaatgt gtatgattta aaatcacaa ataaaatttt atgatctaaa     4440
aaaaaaaaaa aa                                                        4452
```

<210> SEQ ID NO 4
<211> LENGTH: 1025
<212> TYPE: PRT
<213> ORGANISM: Mus musculus

<400> SEQUENCE: 4

Met Ala Gly Val Leu Ser Arg Asp Ala Pro Asp Ile Glu Ser Ile Leu
1               5                   10                  15

Ala Leu Asn Pro Arg Val Gln Ala His Ala Thr Leu Arg Ser Thr Ala
                20                  25                  30

Ala Lys Lys Leu Asp Lys Lys His Trp Lys Arg Asn Thr Asp Lys Asn
            35                  40                  45

Cys Phe Thr Cys Glu Lys Leu Glu Ser Asn Phe Asp Asp Ile Lys His
        50                  55                  60

Thr Thr Leu Gly Glu Arg Gly Ala Leu Arg Glu Ala Val Arg Cys Leu
65                  70                  75                  80

Lys Cys Ala Asp Ala Pro Cys Gln Lys Ser Cys Pro Thr Ser Leu Asp
                85                  90                  95

Ile Lys Ser Phe Ile Thr Ser Ile Ala Asn Lys Asn Tyr Tyr Gly Ala
            100                 105                 110

Ala Lys Leu Ile Phe Ser Asp Asn Pro Leu Gly Leu Thr Cys Gly Met
        115                 120                 125

Val Cys Pro Thr Ser Asp Leu Cys Val Gly Gly Cys Asn Leu His Ala
    130                 135                 140

Ala Glu Glu Gly Pro Ile Asn Ile Gly Gly Leu Gln Gln Phe Ala Thr
145                 150                 155                 160

Glu Val Phe Lys Ala Met Asn Ile Pro Gln Ile Arg Asn Pro Ser Leu

```
                165                 170                 175
Pro Pro Pro Glu His Met Pro Glu Ala Tyr Ser Ala Lys Ile Ala Leu
            180                 185                 190

Phe Gly Ala Gly Pro Ala Ser Ile Ser Cys Ala Ser Phe Leu Ala Arg
            195                 200                 205

Leu Gly Tyr Ser Asn Ile Thr Ile Phe Glu Lys Gln Glu Tyr Val Gly
            210                 215                 220

Gly Leu Ser Thr Ser Glu Ile Pro Gln Phe Arg Leu Pro Tyr Asp Val
225                 230                 235                 240

Val Asn Phe Glu Ile Glu Leu Met Lys Asp Leu Gly Val Lys Ile Ile
            245                 250                 255

Cys Gly Lys Ser Leu Ser Thr Asp Glu Met Thr Leu Ser Ser Leu Lys
            260                 265                 270

Glu Asn Gly Tyr Arg Ala Ala Phe Ile Gly Ile Gly Leu Pro Glu Pro
            275                 280                 285

Lys Lys Asp His Ile Phe Gln Gly Leu Thr Gln Val Gln Gly Phe Tyr
            290                 295                 300

Thr Ser Lys Asp Phe Leu Pro Leu Val Ala Lys Ser Ser Lys Thr Gly
305                 310                 315                 320

Met Cys Ala Cys His Ser Pro Leu Pro Ser Ile Arg Gly Ala Val Ile
            325                 330                 335

Val Leu Gly Ala Gly Asp Thr Ala Phe Asp Cys Ala Thr Ser Ala Leu
            340                 345                 350

Arg Cys Gly Ala Leu Arg Val Phe Ile Val Phe Arg Lys Gly Phe Val
            355                 360                 365

Asn Ile Arg Ala Val Pro Glu Glu Met Glu Leu Ala Lys Glu Glu Lys
            370                 375                 380

Cys Glu Phe Leu Pro Phe Leu Ser Pro Arg Lys Val Ile Val Lys Asp
385                 390                 395                 400

Gly Lys Ile Val Ala Met Gln Phe Val Arg Thr Glu Gln Asp Glu Thr
            405                 410                 415

Gly Asn Trp Val Glu Asp Glu Glu Gln Thr Val Arg Leu Lys Ala Asp
            420                 425                 430

Val Val Ile Ser Ala Phe Gly Ser Val Leu Glu Asp Pro Lys Val Lys
            435                 440                 445

Glu Ala Leu Ser Pro Ile Lys Phe Asn Arg Trp Gly Leu Pro Glu Val
            450                 455                 460

Asn Pro Glu Thr Met Gln Thr Ser Glu Pro Trp Val Phe Ala Gly Gly
465                 470                 475                 480

Asp Val Val Gly Met Ala Asn Thr Thr Val Glu Ser Val Asn Asp Gly
            485                 490                 495

Lys Gln Ala Ser Trp Tyr Ile His Lys His Ile Gln Ala Gln Tyr Gly
            500                 505                 510

Thr Ser Val Pro Ser Gln Pro Thr Met Pro Leu Phe Tyr Thr Pro Val
            515                 520                 525

Asp Leu Val Asp Ile Ser Val Glu Met Ala Gly Leu Arg Phe Pro Asn
            530                 535                 540

Pro Phe Gly Leu Ala Ser Ala Thr Pro Ala Thr Ser Thr Pro Met Ile
545                 550                 555                 560

Arg Arg Ala Phe Glu Ala Gly Trp Gly Phe Ala Leu Thr Lys Thr Phe
            565                 570                 575

Ser Leu Asp Lys Asp Ile Val Thr Asn Val Ser Pro Arg Ile Ile Arg
            580                 585                 590
```

-continued

```
Gly Thr Thr Ser Gly Pro Leu Tyr Gly Pro Gly Gln Ser Ser Phe Leu
            595                 600                 605

Asn Ile Glu Leu Ile Ser Glu Lys Thr Ala Ala Tyr Trp Cys His Ser
610                 615                 620

Val Thr Glu Leu Lys Ala Asp Phe Pro Asp Asn Ile Leu Ile Ala Ser
625                 630                 635                 640

Ile Met Cys Ser Tyr Asn Lys Ser Asp Trp Met Glu Leu Ser Lys Met
                645                 650                 655

Ala Glu Ala Ser Gly Ala Asp Ala Leu Glu Leu Asn Leu Ser Cys Pro
            660                 665                 670

His Gly Met Gly Glu Arg Gly Met Gly Leu Ala Cys Gly Gln Asp Pro
        675                 680                 685

Glu Leu Val Arg Asn Ile Cys Arg Trp Val Arg Gln Ala Val Arg Val
    690                 695                 700

Pro Phe Phe Ala Lys Leu Thr Pro Asn Val Thr Asp Ile Val Ser Ile
705                 710                 715                 720

Ala Arg Ala Ala Lys Glu Gly Gly Ala Asp Gly Val Thr Ala Thr Asn
                725                 730                 735

Thr Val Ser Gly Leu Met Gly Leu Lys Ala Asp Gly Thr Pro Trp Pro
            740                 745                 750

Ala Val Gly Ile Gly Arg Arg Thr Thr Tyr Gly Gly Val Ser Gly Thr
        755                 760                 765

Ala Ile Arg Pro Ile Ala Leu Arg Ala Val Thr Ala Ile Ala Arg Ala
    770                 775                 780

Leu Pro Gly Phe Pro Ile Leu Ala Thr Gly Gly Ile Asp Ser Ala Glu
785                 790                 795                 800

Ser Gly Leu Gln Phe Leu His Ser Gly Ala Ser Val Leu Gln Val Cys
                805                 810                 815

Ser Ala Ile Gln Asn Gln Asp Phe Thr Val Ile Glu Asp Tyr Cys Thr
            820                 825                 830

Gly Leu Lys Ala Leu Leu Tyr Leu Lys Ser Ile Glu Glu Leu Ala Asp
        835                 840                 845

Trp Asp Gly Gln Ser Pro Pro Ile Ile Ser His Gln Lys Gly Lys Pro
    850                 855                 860

Val Pro Arg Val Ala Glu Leu Met Gly Gln Lys Leu Pro Ser Phe Gly
865                 870                 875                 880

Pro Tyr Leu Glu Gln Arg Lys Lys Ile Ile Ala Ala Ser Lys Ile Arg
                885                 890                 895

Gln Lys Asp Gln Asn Thr Ala Cys Ser Pro Leu Gln Arg Lys His Phe
            900                 905                 910

Asn Ser Gln Lys Pro Ile Pro Ala Ile Lys Asp Val Ile Gly Lys Ser
        915                 920                 925

Leu Gln Tyr Leu Gly Thr Phe Gly Glu Met Ser Ile Met Glu Gln Val
    930                 935                 940

Val Ala Leu Ile Asp Glu Glu Met Cys Ile Asn Cys Gly Lys Cys Tyr
945                 950                 955                 960

Met Thr Cys Asn Asp Ser Gly Tyr Gln Ala Ile Gln Phe Asp Pro Glu
                965                 970                 975

Thr His Leu Pro Thr Val Ser Asp Thr Cys Thr Gly Cys Thr Leu Cys
            980                 985                 990

Leu Ser Val Cys Pro Ile Met Asp Cys Ile Arg Met Val Ser Arg Ala
        995                 1000                1005

Thr Pro  Tyr Gln Pro Lys Arg  Gly Leu Pro Leu Ala  Val Lys Pro
    1010                1015                1020
```

Val Cys
    1025

<210> SEQ ID NO 5
<211> LENGTH: 19
<212> TYPE: DNA
<213> ORGANISM: Artificial
<220> FEATURE:
<223> OTHER INFORMATION: Primer

<400> SEQUENCE: 5
cggccctagt ctgcctgtt                                            19

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
gagtctgcca gtgacaaacc ct                                        22

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
aaagccgctc aactacatgg                                           20

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
tgctttgaat gcgtcccaga g                                         21

<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9
aatgattcga agagcttttg aagc                                      24

<210> SEQ ID NO 10
<211> LENGTH: 19
<212> TYPE: DNA
<213> ORGANISM: Artificial
<220> FEATURE:
<223> OTHER INFORMATION: Primer

<400> SEQUENCE: 10
gttccccgga tgattctgg                                            19

<210> SEQ ID NO 11
<211> LENGTH: 33
<212> TYPE: DNA

```
<213> ORGANISM: Artificial
<220> FEATURE:
<223> OTHER INFORMATION: TaqMan probe

<400> SEQUENCE: 11
tgccctcacc aaaactttct ctcttgataa gga                                    33

<210> SEQ ID NO 12
<211> LENGTH: 25
<212> TYPE: DNA
<213> ORGANISM: Artificial
<220> FEATURE:
<223> OTHER INFORMATION: Primer

<400> SEQUENCE: 12
tcacccacac tgtgcccatc tacga                                             25

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
cagcggaacc gctcattgcc aatgg                                             25

<210> SEQ ID NO 14
<211> LENGTH: 26
<212> TYPE: DNA
<213> ORGANISM: Artificial
<220> FEATURE:
<223> OTHER INFORMATION: TaqMan probe

<400> SEQUENCE: 14
atgccctccc ccatgccatc ctgcgt                                            26

<210> SEQ ID NO 15
<211> LENGTH: 19
<212> TYPE: DNA
<213> ORGANISM: Artificial
<220> FEATURE:
<223> OTHER INFORMATION: Primer

<400> SEQUENCE: 15
gaaggtgaag gtcggagtc                                                    19

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
gaagatggtg atgggatttc                                                   20

<210> SEQ ID NO 17
<211> LENGTH: 20
<212> TYPE: DNA
<213> ORGANISM: Artificial
<220> FEATURE:
<223> OTHER INFORMATION: TaqMan probe

<400> SEQUENCE: 17
caagcttccc gttctcagcc                                                   20
```

METHOD FOR PREDICTION OF SENSITIVITY TO 5-FLUOROURACIL-TYPE ANTICANCER AGENT

TECHNICAL FIELD

The present invention relates to a method for predicting sensitivities to 5-fluorouracil-based anticancer agents.

BACKGROUND ART

DNA copy number alterations are one of the many causes which affect gene expression alterations. In recent years, comprehensive search methods using such as array CGH have been employed in the analysis of DNA copy numbers, and such methods have been gradually demonstrated to be useful. An epoch-making article which identified the causative gene for melanoma drug resistance from analyses of NCI60 screening panel cell lines with 100K SNP arrays (Affymetrix) was published in Nature in July last year (Non-Patent Document 1). The raw data contained in the article are disclosed in NCI database and invite re-analysis by the third party. On the other hand, no report has been made about correlation between abnormalities in DNA copy numbers and the efficacies of existing anticancer agents.

To date, as a method for predicting sensitivities to 5-fluorouracil-based anticancer agents, determination of the enzyme activity of dihydropyrimidine dehydrogenase prepared from a cancer cell line or cancer tissue, determination of the quantity thereof by ELISA, or determination of its mRNA expression level has been attempted (Non-Patent Documents 2 and 3, Patent Document 1). However, enzyme or mRNA is easily degraded when fresh tissues from surgical operation are stored. Yet, the degree of degradation varies depending on the laboratory. Thus, it has been difficult to use the enzyme activity, quantity or mRNA expression level as a common indicator for predicting sensitivity. Furthermore, a large amount of tissue is required for determination of enzyme activity, and the amount of sample obtainable from biopsy or the like was insufficient to enable such determination. Besides, determination of mRNA expression levels using paraffin-embedded samples which are widely used in histopathology is difficult in terms of maneuver.

[Non-Patent Document 1]
Integrative genomic analyses identify MITF as a lineage survival oncogene amplified in malignant melanoma: Garraway-L A, et al. Nature (2005) vol. 436, 7 July, pp 117-121

[Non-Patent Document 2]
Dihydropyrimidine dehydrogenase activity in human peripheral blood mononuclear cells and liver; population characteristics, newly identified deficient patients, and clinical implication in 5-fluorouracil chemotherapy: Lu Z, Zhang R, Diasio R B. Cancer Res. 1993 Nov. 15; 53(22):5433-8

[Non-Patent Document 3]
A role for dihydropyrimidine dehydrogenase and thymidylate synthase in tumour sensitivity to fluorouracil: Beck A, Etienne M C, Cheradame S, Fischel J L, Formento P, Renee N, Milano G. Eur J Cancer. 1994; 30A(10): 1517-22

[Patent Document 1]
Japanese Unexamined Patent Publication (PCT) No. 2005-508603

DISCLOSURE OF THE INVENTION

Problem for Solution by the Invention

It is an object of the present invention to analyze a factor which affects sensitivities to anticancer agents and to demonstrate the utility of the factor.

Means to Solve the Problem

The present inventors have comprehensively analyzed the data used in the above-described articles and the drug sensitivity data, gene expression data and karyotype data accumulated enormously in NCI database (data mining) to thereby identify an alteration in DNA copy number which affects sensitivities to existing anticancer agents (in Examples herein, 5-FU-based anticancer agents), the alteration having been unknown to date. The present inventors have also examined whether this finding can be generalized or not using 31 human cancer-derived xenografts (not overlapping the cell lines in the NCI screening panel) obtained through subcutaneous transplantation into nude mice.

The present invention relates to the following inventions.
(1) A method of predicting the sensitivity of a cancer cell to a 5-fluorouracil-based anticancer agent using the copy number of dihydropyrimidine dehydrogenase gene as an indicator.
(2) The method of (1), comprising determining the copy number of dihydropyrimidine dehydrogenase gene in a cancer cell derived from a subject, wherein the subject's sensitivity to the 5-fluorouracil-based anticancer agent is predicted to be high when the resultant copy number is 2 or less and the subject's sensitivity to the 5-fluorouracil-based anticancer agent is predicted to be low when the resultant copy number is more than 2.
(3) The method of (1) or (2), wherein the copy number of dihydropyrimidine dehydrogenase gene is determined by at least one method selected from the group consisting of PCR method, FISH method, array CGH method, DNA microarray method and Southern hybridization method.
(4) The method of any one of (1) to (3), wherein the 5-fluorouracil-based anticancer agent comprises at least one component selected from the group consisting of 5-fluorouracil, tegafur, 5'-deoxy-5-fluorouracil and capecitabine.
(5) A kit for predicting sensitivities to 5-fluorouracil-based anticancer agents, comprising a reagent for determining the copy number of dihydropyrimidine dehydrogenase gene.
(6) The kit according of (5), wherein the reagent for determining the copy number of dihydropyrimidine dehydrogenase gene is oligonucleotide primers capable of specifically amplifying the whole or a part of dihydropyrimidine dehydrogenase gene or an oligo- or poly-nucleotide probe capable of specifically hybridizing to dihydropyrimidine dehydrogenase gene.
(7) A pair of primers composed of an oligonucleotide consisting of the DNA sequence as shown in SEQ ID NO: 5 and an oligonucleotide consisting of the DNA sequence as shown in SEQ ID NO: 6

Effect of the Invention

According to the present invention, it has been found that alteration in the copy number of dihydropyrimidine dehydrogenase gene affects the sensitivity of cancer cells to 5-fluorouracil-based anticancer agents. The present invention is applicable to prediction of subjects' sensitivities to 5-fluorouracil-based anticancer agents.

The present specification encompasses the contents described in the specification and/or drawings of Japanese Patent Application No. 2006-16367 based on which the present patent application claims priority.

BEST MODE FOR CARRYING OUT THE INVENTION

Figure 1:
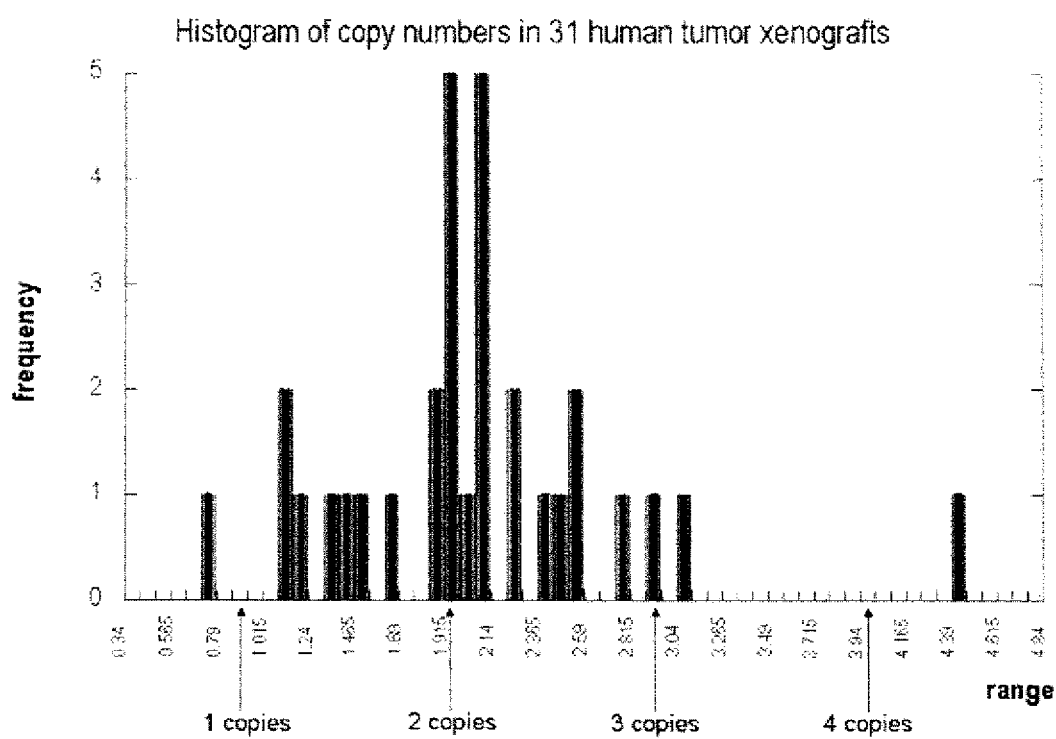
FIG. 1 is a histogram showing the distribution of DPYD copy numbers in 31 xenografts. The vertical axis represents frequency and the horizontal axis represents DPYD copy number.

Hereinbelow, the embodiments of the present invention will be described in detail.

The present invention provides a method of predicting sensitivities to 5-fluorouracil-based anticancer agents (hereinafter, sometimes referred to as "5-FU") using as an indicator the copy number of dihydropyrimidine dehydrogenase gene (hereinafter, sometimes referred to "DPYD") (i.e., the number of the gene contained in one cell).

The term "dihydropyrimidine dehydrogenase" used herein refers to an enzyme with a molecular weight of about 111 kDa (EC 1.3.1.2) which catalyzes antidotal degradation of 5-fluorouracil. This enzyme acts as a rate-limiting enzyme in the pyrimidine degradation pathway. It is known that the activity of this enzyme is high mainly in the liver. Genetic sequence information for this enzyme is registered at the NCBI web site (http://www.ncbi.nlm.nih.gov/) as RefSeq ID: NM_00110 (human) and RefSeq ID: NM_170778 (mouse). The amino acid sequence information thereof is registered in the same database as NP_000101 (human) and NP_740748 (mouse). The nucleotide sequence and amino acid sequence for human-derived dihydropyrimidine dehydrogenase are described in Diasio, R. B. et al., J. Clin. Invest. 81(1), 47-51 (1988). The nucleotide sequence and amino acid sequence for mouse-derived dihydropyrimidine dehydrogenase are described in Porsin, B. et al, Eur. J. Cancer 39 (6), 822-828 (2003).

In one embodiment of the present invention, it is possible to determine the copy number of dihydropyrimidine dehydrogenase gene in a cancer cell derived from a subject and to predict that the subject's sensitivity to 5-fluorouracil-based anticancer agents is high when the copy number is 2 or less and that the subject's sensitivity to 5-fluorouracil-based anticancer agents is low when the copy number is more than 2.

In the present invention, when a cancer cell is judged "highly sensitive" to an anticancer agent, therapeutic efficacies (such as antitumor effect, survival benefit, etc.) resulting from the administration of the anticancer agent are predicted to be high. When a cancer cell is judged "lowly sensitive" to an anticancer agent, therapeutic efficacies are predicted to be low. Therefore, the present invention also includes a method of predicting the therapeutic efficacy of a 5-fluorouracil-based anticancer agent on a cancer using as an indicator the copy number of dihydropyrimidine dehydrogenase gene. More specifically, the present invention also includes a method of predicting the therapeutic efficacy of a 5-fluorouracil-based anticancer agent on a cancer cell using the copy number of dihydropyrimidine dehydrogenase gene as an indicator, comprising determining the copy number of dihydropyrimidine dehydrogenase gene in a cancer cell derived from a subject, wherein the therapeutic efficacy on the subject by the 5-fluorouracil-based anticancer agent is predicted to be high when the resultant copy number is 2 or less and the therapeutic efficacy on the subject by the 5-fluorouracil-based anticancer agent is predicted to be low when the resultant copy number is more than 2.

In the method of the present invention, not only human but also a mammal such as pig, monkey, chimpanzee, dog, cattle, rabbit, rat or mouse may be used as the subject.

For determination of the copy number of dihydropyrimidine dehydrogenase gene in a cancer cell derived from a subject, materials containing cancer tissue or cancer cells (such as biopsy samples, removed organs, paraffin-embedded tissue samples, blood, spinal fluid, lymph, saliva, gastric juice, pancreatic juice, duodenal fluid, intestinal fluid, stool, etc.) or cultured cells or tissues obtainable therefrom may be used.

Specific types of cancer include, but are not limited to, gastric cancer, large bowel cancer, breast cancer, lung cancer, pancreatic cancer, liver cancer, ovarian cancer, prostate cancer, head and neck cancer, malignant lymphoma, leukemia, brain tumor, uterine cancer and bladder cancer.

The copy number of dihydropyrimidine dehydrogenase gene may be determined by PCR method, FISH method, array CGH method, DNA microarray method, Southern hybridization method, or the like.

PCR Method

When the copy number of dihydropyrimidine dehydrogenase gene is determined by PCR method, the following procedures may be used.

Briefly, PCR is performed using as a template the genomic DNA of a cancer cell prepared by phenol chloroform method, centrifuge column method, magnetic beads method or the like. The PCR may be performed using QIAGEN QuantiTect SYBR Green PCR kit and ABI7300 sequence detector under the PCR conditions described below: 1 cycle of 94° C., 15 min and 45 cycles of 94° C., 20 sec; 56° C., 20 sec; and 70° C., 30 sec. However, these conditions may be appropriately changed as long as the experiment can be reproduced. The invention practiced under such changed conditions is also included within the scope of the present invention. The analytical value of the target DNA may be obtained based on the PCR cycle number (Ct value) at which the PCR product reached any threshold value. Further, the gene copy number may be corrected with an analytical value obtained using a reference sequence which varies little in copy number between cancer cells and normal cells. When the copy number of dihydropyrimidine dehydrogenase gene is determined by PCR method, oligonucleotide primers may be used which are capable of specifically amplifying the whole or a part of dihydropyrimidine dehydrogenase gene. These oligonucleotide primers may be primers capable of hybridizing to a region of dihydropyrimidine dehydrogenase gene having a nucleotide sequence which may be present in cancer cells but is not found in other genomic DNA. The primer sizes are preferably about 17-25 bases. Preferably, the Tm values are set uniformly for the forward primer and the reverse primer at about 55-65° C., which is apt to produce good results. A pair of primers which have less complementarity to one another are selected so that the two primers do not anneal to one another. In order to prevent particularly the decrease in amplification efficiency due to formation of primer dimers, the primers are designed so that their 3' end sequences are not complementary to one another in 3 or more consecutive bases. Further, in order to avoid formation of secondary structures within primers, the primers are designed so that they do not contain auto-complementary sequences of 4 or more bases. GC content is set at about 40-60% so that partial GC- or AT-rich sequences are avoided. For achieving stable binding of the 3' ends of primers to the template DNA, the 3' terminal sequences of the primers should not be AT-rich or GC-rich. It should be noted that when the 3' terminal sequence of a primer is GC-rich, non-specific product are easily produced. With respect to the Tm value, the following points should be noted. The "Tm value" refers to the temperature at which 50% of double-stranded DNA is dissociated into single-stranded DNA (melting temperature). In order for primers to anneal to the template DNA to thereby start elongation, the annealing temperature must be set below the primer Tm value. However, excessive lowering of the temperature causes non-specific annealing to thereby decrease specific amplification efficiency. When there are a plurality of candidate primer pairs, usually, a pair with a high Tm value is selected in order to enhance specificity. When two primers making a pair have respective Tm values different from each other, the annealing temperature is tentatively set considering the lower Tm value. When primers have been designed taking into account of the above-described points, good results are obtained with annealing temperatures of 55-65° C. empirically, However, when no PCR product is obtained, PCR should be performed at a lowered temperature. When non-specifically amplified products are obtained, PCR should be performed at a raised temperature.

One example of the nucleotide sequences for a primer pair used in PCR method is given below.

```
Forward primer:
5'-CGGCCCTAGTCTGCCTGTT-3'       (SEQ ID NO: 5)

Reverse primer:
5'-GAGTCTGCCAGTGACAAACCCT-3'    (SEQ ID NO: 6)
```

As a reference genomic sequence, LINE-1 (a sequence occurring abundantly on the genome whose copy number is believed to be almost the same between cancer cells and normal cells) may be used.

```
Forward primer:
5'-AAAGCCGCTCAACTACATGG-3'      (SEQ ID NO: 7)

Reverse primer:
5'-TGCTTTGAATGCGTCCCAGAG-3'     (SEQ ID NO: 8)
```

FISH Method

When the copy number of dihydropyrimidine dehydrogenase gene is determined by FISH method, an oligo- or poly-nucleotide probe capable of specifically hybridizing to dihydropyrimidine dehydrogenase gene may be used. This oligo- or poly-nucleotide probe may be a probe capable of hybridizing to a region of dihydropyrimidine dehydrogenase gene having a nucleotide sequence which may be present in cancer cells but is not found in other genomic DNA.

As the probe for FISH, a DNA fragment, a PCR product, a cDNA, a PAC clone or a BAC clone (each of which has a sequence of interest) may be used. In situ hybridization method has been developed as a method for examining the presence/absence and distribution of a specific DNA or RNA (nucleic acid) in cells or tissues. This method utilizes the nature of a nucleic acid probe having a nucleotide sequence complementary to a specific nucleic acid in cells, i.e., such a probe specifically forms a complex (hybridization). When such probes are labeled with radioisotopes (RIs) or antigenic substances (haptens) in advance, the site of hybridization becomes discriminable. Conventionally, RIs have been used for labeling probes. Recently, however, fluorescence labeling methods or detection methods utilizing non-radioactive substances, e.g., haptens such as biotin or digoxigenin, have been developed. Among them, fluorescence in situ hybridization method called FISH has been developed (Tohyama (ed.). Experimental Medicine Special Issue, "In situ Identification of Proteins and Nucleic Acid Molecules").

Procedures for FISH method will be illustrated below. Chromosome samples may be smears on slide glass prepared from cultured cells of an isolated cancer. Alternatively, chromosome samples may be slide samples sliced from formalin-fixed, paraffin-embedded cancer-containing tissue blocks. After hardening for prevention of falling off from the slide glass during hybridization process, chromosome sample slides are denatured by formamide treatment. In a FISH method where biotin is used as a labeling substance, a probe DNA is labeled with biotin-dUTP (or biotin-dATP) and then the DNA is thermally denatured. Subsequently, the DNA probe is subjected to hybridization to single-stranded DNA. The resultant double-stranded DNA composed of the biotin-labeled DNA and the genomic DNA is washed with a washing solution (major component is SSC buffer) and treated with avidin-FITC solution which has a high affinity to biotin. Subsequently, the double-stranded DNA is washed with a series of SSC buffer, followed by addition of an antibleaching agent thereto drop wise. The resultant DNA is covered with a cover glass, observed under a fluorescence microscopy and photographed.

Array CGH Method

CGH (comparative genomic hybridization) method is an analytical method for specifying a chromosome in which an abnormality is occurring with a fluorescent dye and is one type of FISH method. Conventional CGH method was low in dissolution capacity and it was hard to identify a target gene with the resultant genomic abnormality data. This time, the target genomic region in which copy number abnormalities are to be detected is definite. Therefore, it is possible to detect copy number abnormalities by the CGH method described below. Briefly, DNA is extracted from a cancer cell and a normal cell (used as a control). The cancer cell-derived DNA is labeled with a green fluorescent dye (FITC) and the normal cell-derived DNA is labeled with a red fluorescent dye (Texas red). A mixed solution consisting of equal amounts of the two labeled DNAs is prepared and subjected to hybridization. In conventional CGH method, as samples to be hybridized, chromosome sample slides prepared by taking blood samples from human, culturing them, terminating the cell division at metaphase, and smearing cells on slide glass with the cell membrane being exposed were used. However, by performing CGH using a slide glass with a large number of cloned DNA fragments set in array (array CGH), it is possible to quantitatively determine the copy number of cancer DNA in a region corresponding to a DNA fragment in the array, based on the intensity ratio between fluorescence signals from labeled cancer cell- and normal cell-derived DNAs. Examples of DNAs to be set in array on a slide glass include, but are not limited to, BAC clones which are 100 kb human genomic fragments cloned or products obtained by amplifying cloned genomic fragments by DOP-PR with BAC as a template.

Microarray Method

It is possible to detect alterations in copy number in a specific region in the genome using commercial DNA microarrays (oligonucleotide arrays or cDNA microarrays) for SNP detection in the same manner as in array CGH method. For DNA preparation method and labeling method, standard protocols provided in commercial microarrays may be used.

Southern Hybridization Method

Southern hybridization method is a classic method for detecting a DNA of interest utilizing complementarity in nucleic acid. Briefly, genomic DNAs prepared from a cancer cell and a normal cell are treated with appropriate restriction enzymes and electrophoresed on agarose gel to fractionate depending on the DNA size. After denaturation into single-stranded DNA by alkali denaturation, the resultant DNA is transferred onto a filter (such as nitrocellulose) and fixed. A probe which is a DNA fragment comprising a target sequence labeled with a radioisotope or the like is reacted with the filter. Thus, it is possible to detect alterations in copy number of a genetic region of interest.

The copy number of dihydropyrimidine dehydrogenase gene may be determined by any of the above-described methods. When the copy number of dihydropyrimidine dehydrogenase gene is 2 or less, it is possible to predict that the subject's sensitivity to 5-fluorouracil-based anticancer agents is high. When the copy number of dihydropyrimidine dehydrogenase gene is more than 2, it is possible to predict that the subject's sensitivity to 5-fluorouracil-based anticancer agents is low. If it is possible to predict the sensitivity of a cancer patient to 5-fluorouracil-based anticancer agents, selection of appropriate drugs or avoidance of unnecessary drug administration becomes possible in cancer treatment. Thus, it becomes possible to make an appropriate administration plan or to change to an appropriate administration plan.

The method of the present invention has the following advantages. By using as a material DNA which is unlikely to undergo degradation and by using a universal indicator (gene copy number), the method of the present invention enables prediction of sensitivities to 5-FU-based anticancer agents with DPYD as a standardized indicator among various laboratories. Further, by using a wide range of samples including paraffin-embedded samples as a material, prediction of sensitivities can be practiced easily.

Specific examples of 5-fluorouracil-based anticancer agents include single drugs and combined drugs such as 5-fluorouracil, tegafur, 5'-deoxy-5-fluorouracil, capecitabine, UFT (combined drug comprising tegafur and uracil at a molar ratio of 1:4), TS-1 (combined drug comprising tegafur, gimeracil and oteracil potassium at a molar ratio of 1:0.4:1), carmofur, yamaful and sunfural. Among all, anticancer agents comprising at least one component selected from the group consisting of 5-fluorouracil, tegafur, 5'-deoxy-5-fluorouracil and capecitabine are preferred.

The present invention also provides a kit for predicting sensitivities to 5-fluorouracil-based anticancer agents, comprising a reagent for determining the copy number of dihydropyrimidine dehydrogenase gene.

As the reagent for determining the copy number of dihydropyrimidine dehydrogenase gene, oligonucleotide primers capable of specifically amplifying the whole or a part of dihydropyrimidine dehydrogenase gene, an oligo- or polynucleotide probe capable of specifically hybridizing to dihydropyrimidine dehydrogenase gene, or the like may be given. These primers and probes are as described above. The kit of the present invention may further comprise other reagents, buffers and handling manuals necessary for determination of the copy number of dihydropyrimidine dehydrogenase gene by PCR method, FISH method, array CGH method, DNA microarray method, Southern hybridization method or the like. It is preferred that the handling manual describe criteria for predicting sensitivities to 5-fluorouracil-based anti-cancer agents in addition to how to use the kit.

Further, the present invention provides a pair of primers composed of an oligonucleotide consisting of the DNA sequence as shown in SEQ ID NO: 5 and an oligonucleotide consisting of the DNA sequence as shown in SEQ ID NO: 6. By using the pair of primers of the present invention, it is possible to determine by PCR method the copy number of dihydropyrimidine dehydrogenase gene in a cancer cell derived from a subject and to predict the subject's sensitivity to 5-fluorouracil-based anti-cancer agents based on the results of the determination.

EXAMPLES

Hereinbelow, the present invention will be described in more detail with reference to the following Examples. However, the present invention is not limited to these Examples.

Example 1

Examination in Human Tumor Strains Subcutaneously Transplanted into Nude Mice

As a result of deep data-mining of the NCI60 profiling data, the present inventors have found abnormalities in the copy number of a gene that affect sensitivities to 5-FU. As an independent data set for examining whether this finding can be generalized or not, in vivo human tumor strains (xenografts: various organ cancer-derived 31 strains subcultured through subcutaneous transplantation into nude mice) were used. Particulars of the 31 xenografts are 6 gastric cancer strains (AZ-521, SC-2, ST-40, 4-1ST, SC-4 and OCUM-2MD3), 6 large bowel cancer strains (KM12C, HCT-15, KM20C, COL-1, KM12C/FU and CO-3), 6 breast cancer strains (MC-5, H-31, MC-2, MX-1, MDA-MB-435SHM and MDA-MD-231), 7 lung cancer strains (GT3TKB, LC-11, Lu-99, LX-1, LC-6, Lu-134 and Lu-130) and 6 pancreatic cancer strains (PAN-3, PAN-4, PAN-12, H-48, MIAPaCa-2 and BxPC-3). The suppliers of these cancer strains are as described below. KM12C and KM20C were provided by Dr. Morikawa (National Cancer Institute). KM12C/FU is a strain in which FU resistance was induced in vivo. MDA-MB-435SHM is a high lung metastasis strain created by transplanting a cell line purchased from ATCC into the mammary gland of SCID mouse in vivo. LX-1 and MX-1 were provided by Dr. Inoue (Cancer Chemotherapy Center of JFCR); H-31 and H48 were provided by Dr. Taguchi (Osaka University). AZ-521 and MDA-MB-231 were purchased from Human Science Research Resource Bank and ATCC, respectively HCT-15 and BxPc-3 were purchased from Dainippon Pharmaceutical. The other strains were purchased from Central Institute for Experimental Animals. These tumor sections and cell suspensions were subcutaneously transplanted into nude mice (Male BALB/c-nu/nu nude mice; 5-week old; body weights 18 to 20 g) (purchased from CLEA Japan, Inc.). When the tumor volume (0.5×length×width$^2$) reached 100-300 mm$^3$, 5 mice were allocated to each test group by stratified random allocation using tumor volume as an indicator (day 0). It was confirmed that there was no significant difference in tumor volume between groups. 5-FU-based anticancer agents of UFT, TS-1, 5'-DFUR and Capecitabine were administered orally at the optimal dose (MTD) of each agent for two weeks to thereby determine antitumor effects. The antitumor effect was obtained by examining to what extent the tumor weight of drug-administered mice was inhibited at day 15 as compared to the weight of subcutaneous tumor in control mice which received no drug treatment. Briefly, tumor growth inhibition ratio IR % was calculated by the following formulas. Every experiment was performed in accordance with the ethic guideline concerning animal experiments.

$RTV$=(tumor weight at day 15 of treatment)/(tumor weight before treatment)

IR %=(1−mean $RTV$ in treatment group/mean $RTV$ in control group)×100

In order to obtain the copy number of DPYD gene, primers with the following sequences were designed.

```
Forward primer:
5'-CGGCCCTAGTCTGCCTGTT-3'          (SEQ ID NO: 5)

Reverse primer:
5'-GAGTCTGCCAGTGACAAACCCT-3'       (SEQ ID NO: 6)
```

As a reference genomic sequence, LINE-1 (a sequence occurring abundantly on the genome whose copy number is believed to be almost the same between cancer cells and normal cells) may be used.

```
Forward primer:
5'-AAAGCCGCTCAACTACATGG-3'         (SEQ ID NO: 7)

Reverse primer:
5'-TGCTTTGAATGCGTCCCAGAG-3'        (SEQ ID NO: 8)
```

The gDNA of each xenograft was prepared using QIAAMP DNA mini kit (Qiagen Inc., Valencia, Calif.) according to the manufacturer's instructions.

PCR reaction was performed using QIAGEN QuantiTect SYBR Green PCR kit and ABI7300 sequence detector under the PCR conditions described below: 1 cycle of 94° C., 15 min and 45 cycles of 94° C., 20 sec; 56° C., 20 sec; and 70° C., 30 sec.

The analytical value of the target DNA was calculated from a regression equation created by preparing calibration curves based on the PCR cycle number (Ct value) at which the PCR product reached any threshold value. Further, the gene copy number was calculated by the following formula.

($T$(DPYD)/$T$(LINE-1))/($C$(DPYD)/$C$(LINE-1))×2

(wherein T is the analytical value of DPYD or LINE-1 in the target tumor DNA; and C is the analytical value of DPYD or LINE-1 in the human (male) normal tissue-derived genomic DNA used as a control.)

The total RNA from each xenograft was prepared from a tissue with a wet weight of 20-30 mg using RNeasy (Qiagen Inc., Valencia, Calif.) according to the manufacturer's instructions.

Quantitative determination of DPYD mRNA was performed by TaqMan real-time reverse transcription PCR using TaqMan EZ RT-PCR kit and ABI Prism sequence detector. Standard curves were prepared with serial dilutions of the total RNA from MiaPaCa-2. As internal standards, GAPD and ACTB were quantitatively determined at the same time. The quantity of DPYD mRNA was corrected using the geometric means of both GAPD and ACTB.

Sequences for PCR primers and TaqMan probes are described below.

```
DPYD
5'-AATGATTCGAAGAGCTTTTGAAGC-3' (forward primer)           (SEQ ID NO: 9)

5'-GTTCCCCGGATGATTCTGG-3' (reverse primer)               (SEQ ID NO: 10)

5'-TGCCCTCACCAAAACTTTCTCTCTTGATAAGGA-3' (TaqMan probe),  (SEQ ID NO: 11)
PCR amplification size: 108 bp ACTB
5'-TCACCCACACTGTGCCCATCTACGA-3' (forward primer)         (SEQ ID NO: 12)

5'-CAGCGGAACCGCTCATTGCCAATGG-3' (reverse primer)         (SEQ ID NO: 13)

5'-ATGCCCTCCCCCATGCCATCCTGCGT-3' (TaqMan probe),         (SEQ ID NO: 14)
PCR amplification size: 295 bp
```

```
GAPD
5'-GAAGGTGAAGGTCGGAGTC-3'  (forward primer)           (SEQ ID NO: 15)

5'-GAAGATGGTGATGGGATTTC-3' (reverse primer)           (SEQ ID NO: 16)

5'-CAAGCTTCCCGTTCTCAGCC-3' (TaqMan probe),            (SEQ ID NO: 17)
PCR amplification size: 226 bp
```

PCR reaction conditions were 1 cycle of 50° C., 2 min; 1 cycle of 60° C., 30 min; 1 cycle of 95° C., 5 min; and 45 cycles of 94° C., 20 sec and 60° C., 1 min.

Enzyme Activity of Dihydropyrimidine Dehydrogenase

The enzyme activity of dihydropyrimidine dehydrogenase was determined by the following method. Briefly, 4 volumes of homogenization buffer [20 mM potassium phosphate (pH 8.0) containing 1 mM EDTA and 1 mM β-mercaptoethanol] was added to a tumor tissue, and the resultant mixture was sonicated. The homogenate was centrifuged at 105,000 g for 1 hour at 4° C. and the resultant supernatant was collected. Enzyme reaction was performed with the following composition; 10 mM potassium phosphate (pH 8.0), 0.5 mM EDTA, 0.5 mM β-mercaptoethanol, 2 mM dithiothreitol, 5 mM $MgCl_2$ and 20 μM [6-$^{14}$C] 5-FU.

100 μM NADPH and 25 μl of cell supernatant (reaction volume; 50 μl) were incubated at 37° C. for 30 min. After the reaction, 5 μl of the reaction solution was subjected to thin layer chromatography (Silica gel $60_{F254}$; Merck, Germany) and developed with a mixed solution of ethanol and 1 M ammonium acetate (5:1, v/v). Dihydropyrimidine dehydrogenase activity was determined by measuring the sum of dihydrofluorouracil and 2-fluoro-β-alanine dissociated from [6-$^{14}$C] 5-FU with a liquid scintillation counter. Drugs used: UFT, TS-1 and capecitabine were synthesized by Taiho Pharmaceutical Co., Ltd. 5'-DFUR was purchased from Roche Japan. [6-$^{14}$C]-5-FU (1.85 GBq/mmol) was purchased from Moravek Biochemicals, Inc. (Brea, Calif., USA).

Experimental Results

In order to examine whether the novel finding in NCI60 cells (i.e., correlation between the copy number of DPYD gene and sensitivity to 5-FU) is a phenomenon that may occur generally or not, similar examination was performed in 31 human cancer-derived xenografts obtained by subcutaneous transplantation into nude mice which do not overlap NCI60 cell strains (except for 1 xenograft).

The copy number of DPYD gene in the 31 xenografts distributed widely from 0.78 to 4.4, though the copy number was around 2 in many xenografts (Table 1, FIG. 1).

Figure 2:
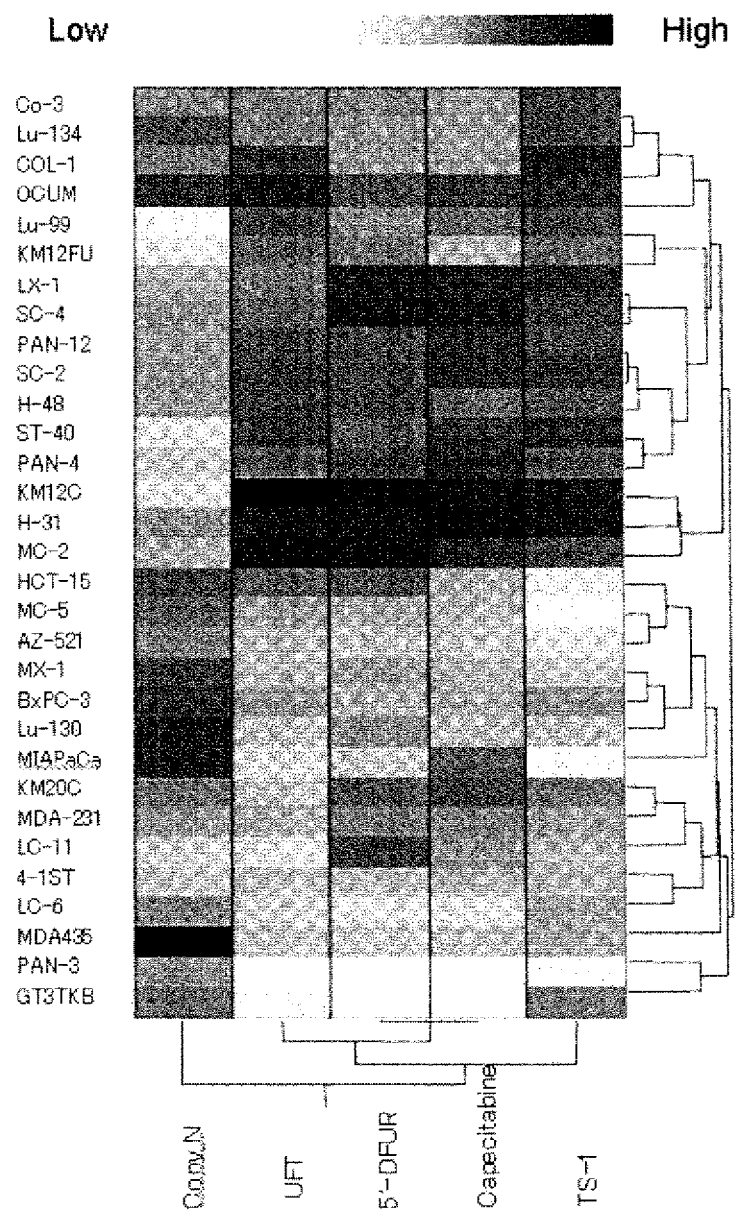
FIG. 2 is a heat map obtained by normalizing the data on the DPYD copy numbers and the sensitivities to FU-based anticancer agents (UFT, TS-1, capecitabine and 5'-DFUR) of 31 xenografts and then clustering with Ward's method. The results are shown in grey scale images. The higher the copy number and the sensitivity are, the darker the color is.

Correlation between the copy number of DPYD gene in the 31 xenografts and the efficacy of anticancer agents (UFT, TS-1, 5'-DFUR and capecitabine) therein was examined. FIG. 2 shows a heat map of the copy number and in vivo efficacy data.

Figure 3:
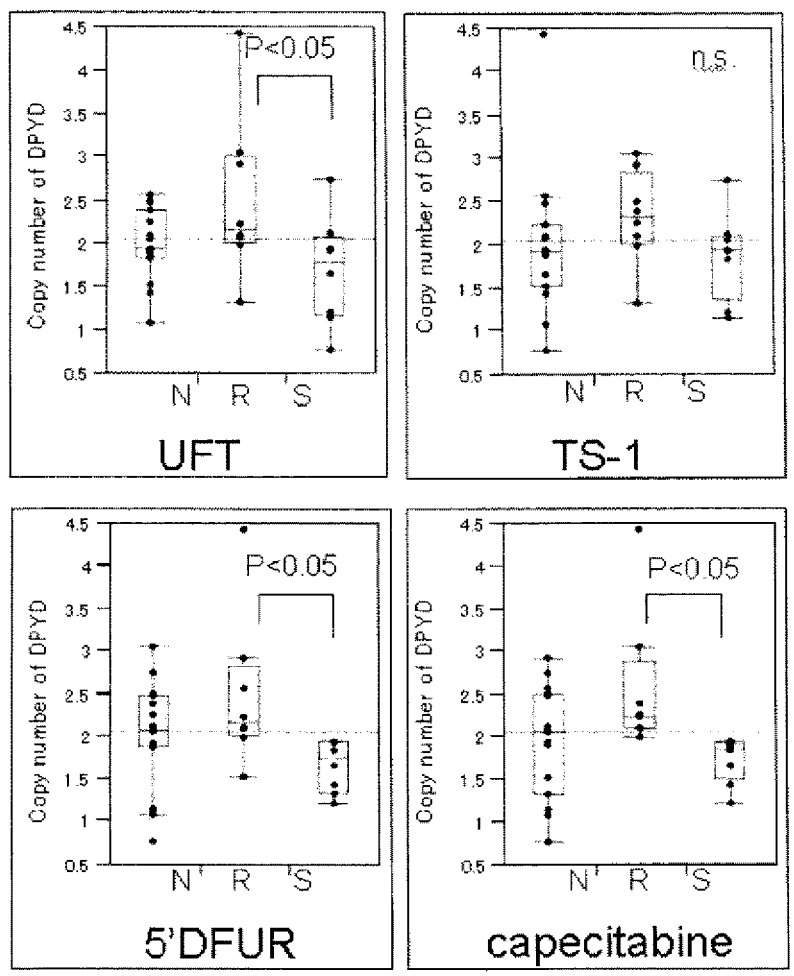
FIG. 3 shows box-and-whisker plots obtained by classifying 31 xenografts with DPYD copy numbers (vertical axis) and sensitivities to the individual drugs indicated below (horizontal axis). Specifically, 31 xenografts were classified into the following three groups based on their sensitivities to 5-FU-based anticancer agents (UFT, TS-1, capecitabine and 5'-DFUR): (S) high sensitivity strains within the 25th percentile, (R) low sensitivity strains which are the 75th percentile or below, and (N) intermediate strains other than the above two groups. A round robin test considering multiplicity was performed by Tukey-Kramer HSD test. The results are shown as P values.

As a result of unsupervised-2-way clustering, the copy number and the in vivo efficacy showed mutually contradictory patterns. Then, the inventors ranked the 31 xenografts according to their sensitivities to drugs. Xenografts within the highest 25th percentile were classified into high sensitivity group; 75th percentile or below were classified into low sensitivity group; and the other xenografts were classified into intermediate group. In each of these three groups, Tukey-Kramer HSD test was performed against the copy number of DPYD gene (FIG. 3). As a result, a significant alteration in copy number was recognized between the high sensitivity group and the low sensitivity group with respect to UFT, 5'-DFUR and capecitabine. That is, the copy number of DPYD gene in the low sensitivity group was significantly higher than the copy number in the high sensitivity group (P<0.05). Although no significant difference was observed with respect to TS-1, a significance tendency was recognized.

Figure 4:
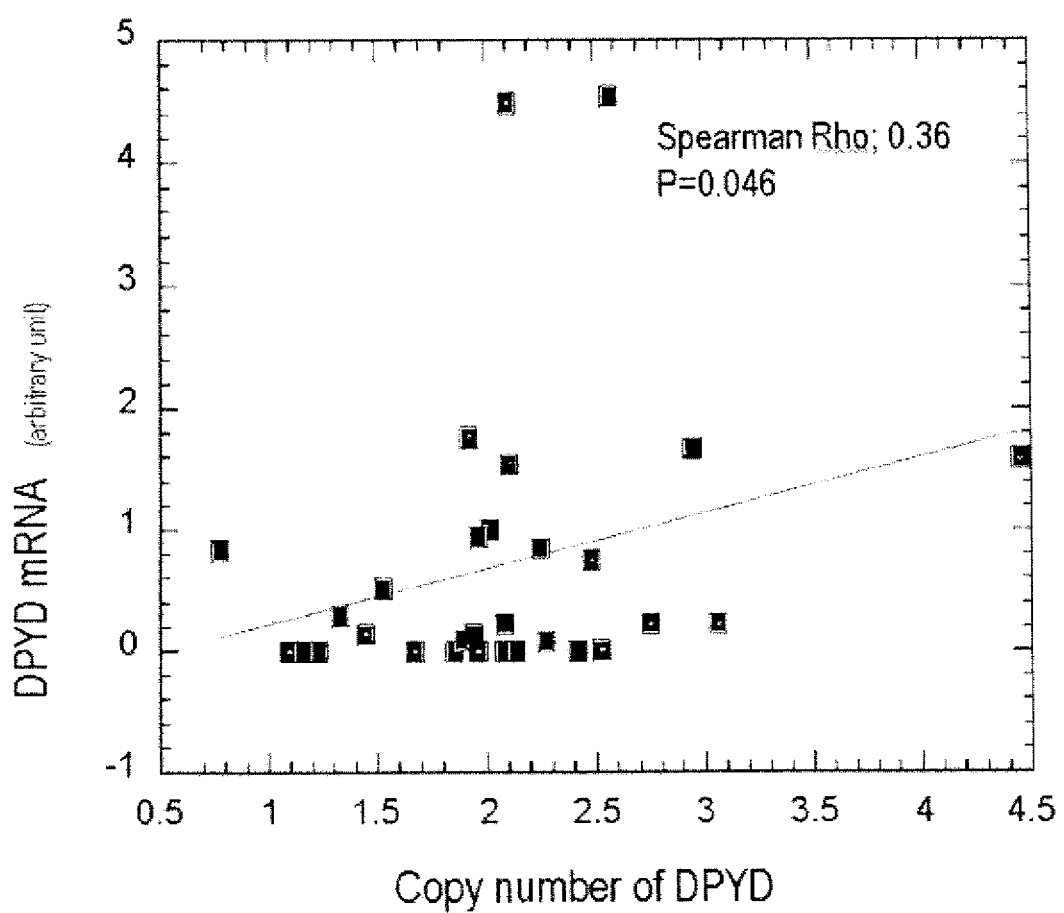
FIG. 4 is a graph plotting correlation between the DPYD copy numbers and DPYD mRNA expression levels in 31 xenografts. The vertical axis represents DPYD copy number and the horizontal axis represents mRNA expression level. Correlation coefficient and significance were obtained using Speaman rank correlation.
Figure 5:
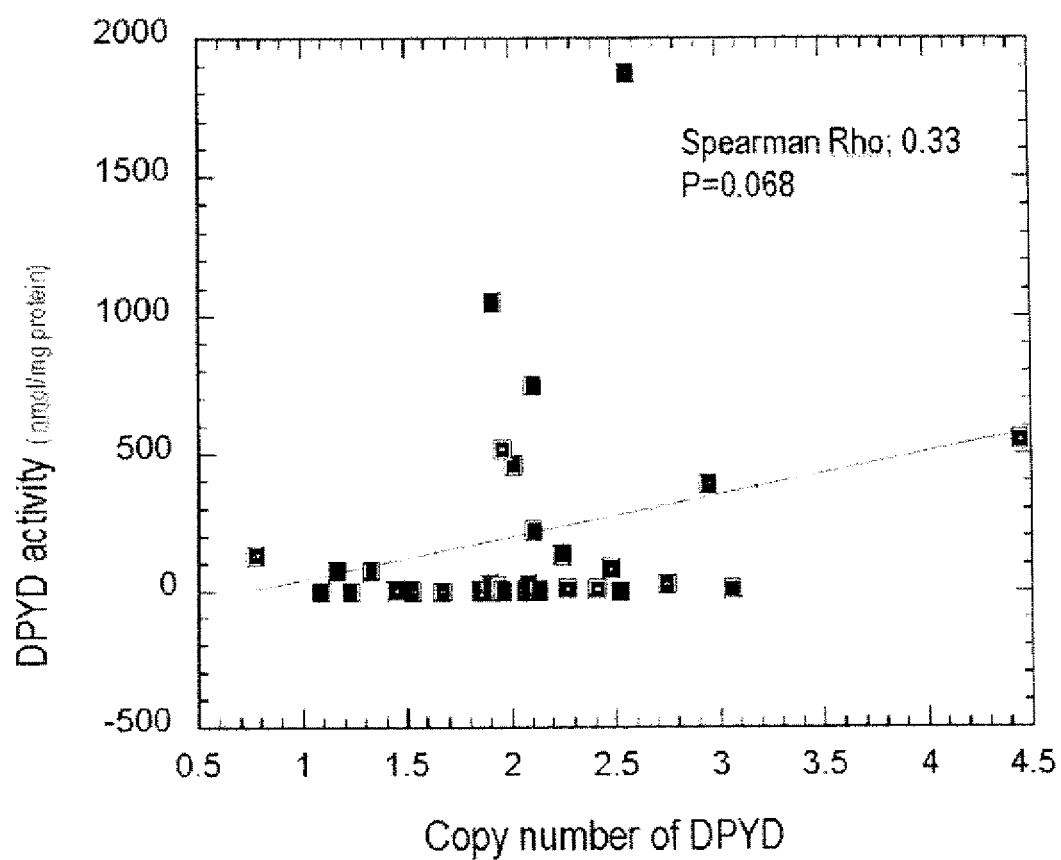
FIG. 5 is a graph plotting correlation between the DPYD copy numbers and DPYD enzyme activity levels in 31 xenografts. The vertical axis represents DPYD copy number and the horizontal axis represents DPYD enzyme activity level. Correlation coefficient and significance were obtained using Speaman rank correlation.

In NCI60 screening cell strains, a significant positive correlation was observed between the copy number of DPYD gene and the expression of DPYD mRNA. In order to examine whether this finding is also applicable to the 31 xenografts or not, correlation between the copy number of DPYD gene and the expression of DPYD mRNA was investigated in the xenografts. The results revealed a significant correlation between them (Spearman Rho=0.36, p=0.046) (FIG. 4). When correlation between the copy number and the DPYD enzyme activity was examined, a positive correlation tendency (P<0.07) was recognized (FIG. 5)

TABLE 1

| Xeno_Name | Copy_Number | SE |
|---|---|---|
| Co-3 | 2.071 | 0.571 |
| HCT-15 | 2.410 | 0.428 |
| KM12C | 1.226 | 0.132 |
| KM20C | 2.080 | 0.313 |
| LC-11 | 1.326 | 0.178 |
| Lu-99 | 0.772 | 0.263 |
| LX-1 | 1.846 | 0.354 |
| MC-2 | 1.668 | 0.219 |
| MX-1 | 2.519 | 0.587 |
| PAN-12 | 1.895 | 0.238 |
| PAN-3 | 2.009 | 0.372 |
| SC-2 | 1.935 | 0.298 |
| ST-40 | 1.159 | 0.163 |
| 4-1ST | 1.526 | 0.425 |
| SC-4 | 1.934 | 0.492 |
| COL-1 | 2.132 | 0.359 |
| MDA435 | 4.449 | 2.690 |
| BxPC-3 | 2.571 | 0.379 |
| Lu-130 | 3.060 | 0.670 |
| KM12FU | 1.086 | 0.171 |
| LC-6 | 2.101 | 0.402 |
| MIAPaCa | 2.944 | 0.402 |
| MDA-231 | 1.919 | 0.316 |
| Lu-134 | 2.480 | 0.623 |
| GT3TKB | 2.243 | 0.260 |
| OCUM | 2.745 | 0.308 |
| MC-5 | 2.268 | 0.403 |
| H-31 | 1.957 | 0.187 |
| H-48 | 1.960 | 0.198 |
| PAN-4 | 1.448 | 0.277 |
| AZ-521 | 2.102 | 0.365 |

Reference DNA: promega human (male) genomic DNA=2 copies
Mean and standard error from 3 independent experiments.

Example 2

Examination with Formalin-Fixed Paraffin Sections of Human Tumor Strains

The present invention is expected to provide a method for predicting sensitivities to anticancer agents which is widely applicable clinically and yet highly reliable. One of the major reasons for this expectation resides in a point that formalin-fixed paraffin-embedded samples stored in clinical scenes for histopathological examination are believed to be useful as test materials. Then, the present inventors examined whether or not it is possible to detect the copy number of DPD gene by FISH method using paraffin-embedded tissue samples as test materials. As experimental materials, in vivo human tumor strains (Lu-130 and PAN-4) were used. Slide samples (5 μm thick) cut out from paraffin blocks were subjected to deparaffinization and dried. These slide samples were dipped in PBS for 5 min, protease-treated in pepsin/0.1 M HCl at 37° C., washed with PBS sufficiently and then dehydrated and dried with 70% and 100% ethanol.

A probe for detecting DPD gene was prepared as described below. Briefly, a vector (pBeloBAC11; Funakoshi) containing a BAG clone with a DPD gene region (clone ID: CTD-3236P20 (Open Biosystems)) was transfected into *Escherichia coli* (DH10B; Funakoshi), which was then cultured for expansion. From the resultant cells, BAC DNA was isolated. Cy3-dUTP was allowed to be taken into BAC DNA by nick translation to thereby prepare 1p21 BAC DNA probe. It was confirmed that this probe produces a signal at an appropriate position of the short arm on chromosome 1 using chromosomal samples (Chromosome Science Labo, Ltd.).

This probe was applied to the samples pre-treated as described above. Then, the samples were denatured for 13 min on a hot plate at 90° C., followed by hybridization overnight at 37° C. As a buffer, a solution containing 50% formamide, yeast tRNA, salmon sperm DNA and 2×SSC. Hybridized samples were washed with 50% formaldehyde/2×SSC and 1×SSC, counterstained with DAPI and mounted with an anti-bleaching agent, followed by detection of probe signals. For signal detection and data analysis, Leica CW4000 System (Leica) was used.

Experimental Results
Verification of DNA Probe

Figure 6:
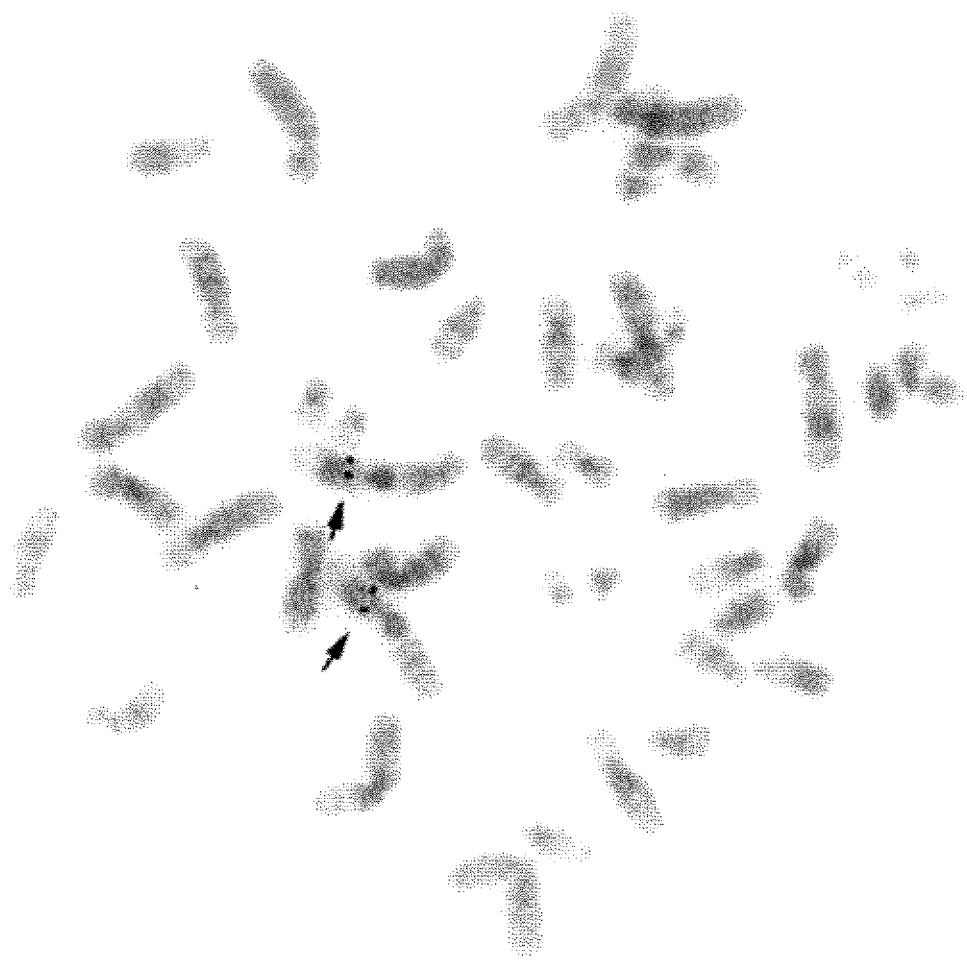
FIG. 6 shows verification of a DNA probe using chromosome samples (mitotic phase). Arrow marks indicate a DPD gene (1p21) probe.

When the probe was mapped on chromosome samples which had undergone Hoechst G-banding, the probe was mapped at around 1p21 or 1p22, each of which is an appropriate genomic region for DPD gene. Thus, good signals were detected (FIG. 6).

FISH Analysis with Paraffin-Embedded Sections

Figure 7:
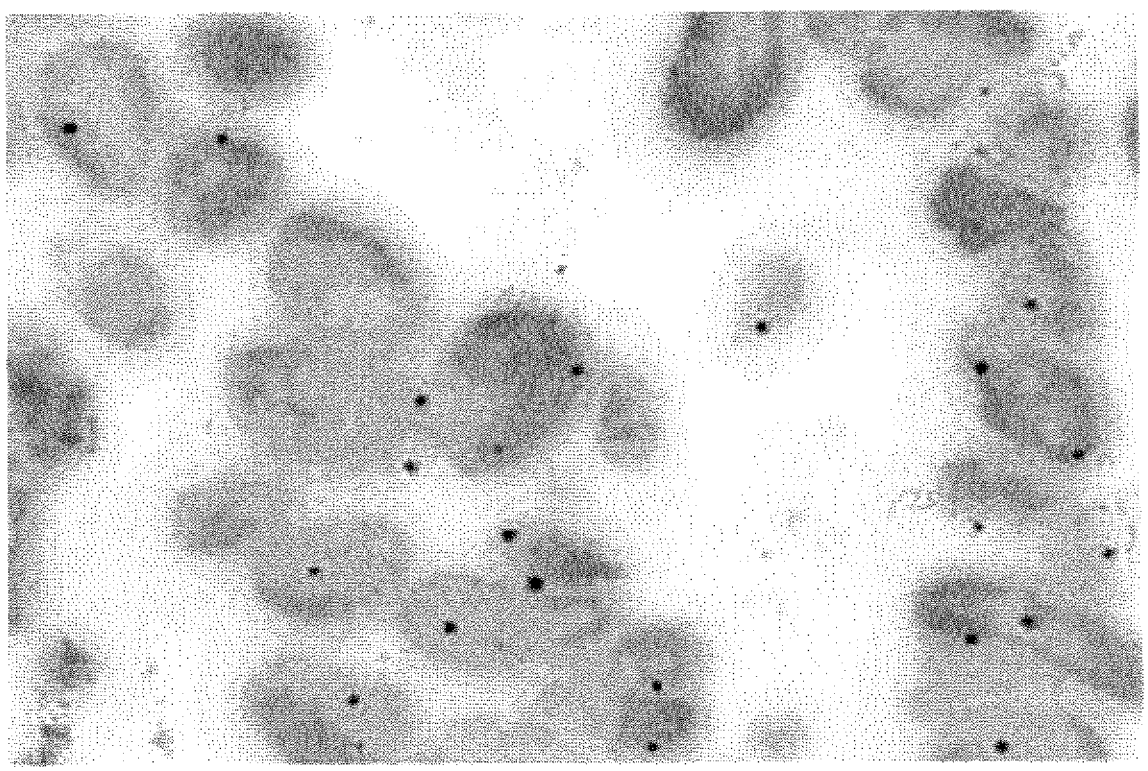
FIG. 7 shows the results of FISH analysis using paraffin samples (PAN-4).
Figure 8:
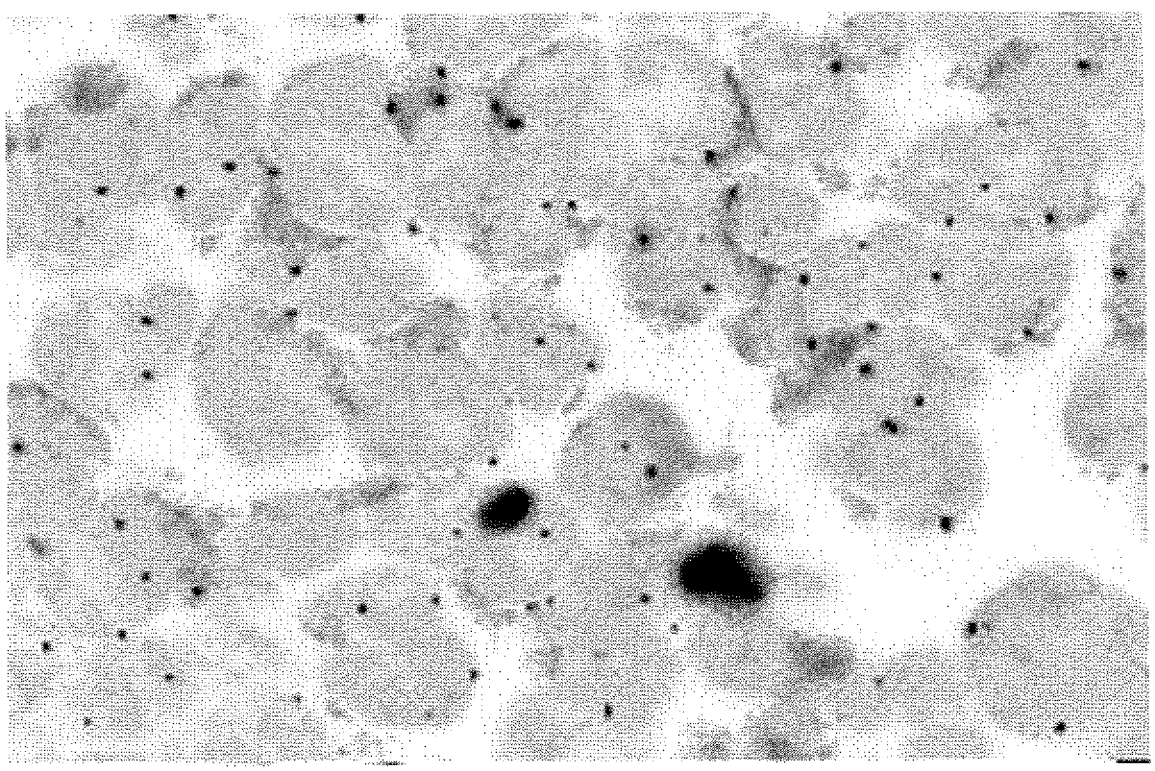
FIG. 8 shows the results of FISH analysis using paraffin samples (Lu-130).

FISH images obtained from human tumor strains PAN-4 and Lu130 are shown in FIGS. 7 and 8. In both samples, clear signals could be obtained. Further, good images with low background were obtained. Out of the counterstained nuclei, 50 or more nuclei which were well isolated on the image were counted. Then, the copy number of DPD gene per cell was determined. In Lu130, 2.3 signals/nucleus were detected. In PAN-4, 1.4 signals/nucleus were detected. These values show a tendency similar to those values obtained in real-time PCR (3.1 and 1.5) (Example 1). Thus, it was shown that the detection results by FISH are reasonable. That is, according to the signal value by FISH method, the DPD gene number in Lu130 was more than 2 copies per cell and therefore this tumor's sensitivity to 5-FU-based anticancer agents was predicted to be low. Likewise, the DPD gene number in PAN-4 was less than 2 copies per cell and therefore this tumor's sensitivity to 5-FU-based anticancer agents was predicted to be high. These predictions and the results of in vivo antitumor effects (Example 1) were consistent in all of the 4 drugs tested in Lu-130; and consistent in 3 drugs out of the 4 drugs tested in PAN-4.

All publications, patents and patent applications cited herein are incorporated herein by reference in their entirety.

INDUSTRIAL APPLICABILITY

The present invention has found that the copy number of DPYD gene affects sensitivities to 5-FU-based antitumor agents. With this finding, it has become possible to predict the sensitivity of a subject to 5-FU-based antitumor agents. The prediction result is applicable to cancer therapy.

SEQUENCE LISTING FREE TEXT

<SEQ ID NO: 1>
SEQ ID NO: 1 shows the DNA sequence of human-derived DPYD.
<SEQ ID NO: 2>
SEQ ID NO: 2 shows the amino acid sequence of human-derived DPYD.
<SEQ ID NO: 3>
SEQ ID NO: 3 shows the DNA sequence of mouse-derived DPYD.
<SEQ ID NO: 4>
SEQ ID NO: 4 shows the amino acid sequence of mouse-derived DPYD.
<SEQ ID NO: 5>
SEQ ID NO: 5 shows the DNA sequence of the forward primer used to determine the copy number of DPYD gene.
<SEQ ID NO: 6>
SEQ ID NO: 6 shows the DNA sequence of the reverse primer used to determine the copy number of DPYD gene.
<SEQ ID NO: 7>
SEQ ID NO: 7 shows the DNA sequence of the forward primer used to determine the copy number of reference genomic sequence LINE-1.
<SEQ ID NO: 8>
SEQ ID NO: 8 shows the DNA sequence of the reverse primer used to determine the copy number of reference genomic sequence LINE-1.
<SEQ ID NO: 9>
SEQ ID NO: 9 shows the DNA sequence of the forward primer used to quantitatively determine DPYD mRNA.
<SEQ ID NO: 10>
SEQ ID NO: 10 shows the DNA sequence of the reverse primer used to quantitatively determine DPYD mRNA.
<SEQ ID NO: 11>
SEQ ID NO: 11 shows the DNA sequence of the TaqMan probe used to quantitatively determine DPYD mRNA.
<SEQ ID NO: 12>
SEQ ID NO: 12 shows the DNA sequence of the forward primer used to quantitatively determine ACTB as an internal standard.
<SEQ ID NO: 13>
SEQ ID NO: 13 shows the DNA sequence of the reverse primer used to quantitatively determine ACTB as an internal standard.
<SEQ ID NO: 14>
SEQ ID NO: 14 shows the DNA sequence of the TaqMan probe used to quantitatively determine ACTB as an internal standard.
<SEQ ID NO: 15>
SEQ ID NO: 15 shows the DNA sequence of the forward primer used to quantitatively determine GAPD as an internal standard.
<SEQ ID NO: 16>
SEQ ID NO: 16 shows the DNA sequence of the reverse primer used to quantitatively determine GAPD as an internal standard.
<SEQ ID NO: 17>
SEQ ID NO: 17 shows the DNA sequence of the TaqMan probe used to quantitatively determine GAPD as an internal standard.

The invention claimed is:

1. A method of predicting the sensitivity of a cancer cell to a 5-fluorouracil-based anticancer agent using the copy number of dihydropyrimidine dehydrogenase gene as an indicator, comprising:
providing a reagent for hybridizing to a region of dihydropyrimidine dehydrogenase gene present in cancer cells but not found in other genomic DNA;
reacting the reagent with dihydropyrimidine dehydrogenase gene in cancer cells derived from a subject; and
generating data based on the reaction with dihydropyrimidine dehydrogenase for correlating the copy number of dihydropyrimidine dehydrogenase gene to the subject's sensitivity to the 5-fluorouracil-based anticancer agent,
wherein the reagents are a pair of oligonucleotide primers represented by SEQ ID NO: 5 and SEQ ID NO: 6.

2. A method of predicting the sensitivity of a cancer cell to a 5-fluorouracil-based anticancer agent, comprising:
providing a reagent for hybridizing to a region of dihydropyrimidine dehydrogenase gene present in cancer cells but not found in other genomic DNA;
reacting the reagent with dihydropyrimidine dehydrogenase gene in cancer cells derived from a subject;
generating data based on the reaction with dihydropyrimidine dehydrogenase for determining the copy number of dihydropyrimidine dehydrogenase gene as an indicator of subject's sensitivity to the 5-fluorouracil-based anticancer agent; and
correlating the determined copy number to the 5-fluorouracil-based anticancer agent based on statistical analysis of the sensitivity of the cancer cells to the 5-fluorouracil-based anticancer agent, wherein the sensitivity is determined to be high for the resultant copy number of 2 or less and to be low for the resultant copy number of more than 2,
wherein the reagent is oligonucleotide primers for amplifying the whole or a part of dihydropyrimidine dehydrogenase gene which the length is about 17 to 25 bases, the primers are configured so that their 3' end sequences are not complementary to one another to prevent dimerization and so that they do not contain auto-complementary sequences of 4 or more bases to avoid formation of secondary structures within the primers, and
wherein a pair of the oligonucleotide primers is represented by SEQ ID NO: 5 and SEQ ID NO: 6.

3. A method of predicting the sensitivity of a cancer cell to a 5-fluorouracil-based anticancer agent, comprising:
providing a reagent for hybridizing to a region of dihydropyrimidine dehydrogenase gene present in cancer cells but not found in other genomic DNA;
reacting the reagent with dihydropyrimidine dehydrogenase gene in cancer cells derived from a subject;
generating data based on the reaction with dihydropyrimidine dehydrogenase for determining the copy number of dihydropyrimidine dehydrogenase gene as an indicator of subject's sensitivity to the 5-fluorouracil-based anticancer agent;
correlating the determined copy number to the 5-fluorouracil-based anticancer agent based on statistical analysis of the sensitivity of the cancer cells to the 5-fluorouracil-based anticancer agent, wherein the sensitivity is determined to be high for the resultant copy number of 2 or less and to be low for the resultant copy number of more than 2; and
correcting the copy number using data obtained from a reference sequence that varies little in copy number between cancer cells and normal cells,
wherein the reference sequence is represented by a pair of forward primer and reverse primer, SEQ ID NO: 7 and SEQ ID NO: 8, respectively.

4. A method of predicting the sensitivity of a cancer cell to a 5-fluorouracil-based anticancer agent, comprising:
providing a reagent for hybridizing to a region of dihydropyrimidine dehydrogenase gene present in cancer cells but not found in other genomic DNA;
reacting the reagent with dihydropyrimidine dehydrogenase gene in cancer cells derived from a subject;
generating data based on the reaction with dihydropyrimidine dehydrogenase for determining the copy number of dihydropyrimidine dehydrogenase gene as an indicator of subject's sensitivity to the 5-fluorouracil-based anticancer agent;
correcting the copy number using data obtained from a reference sequence that varies little in copy number between cancer cells and normal cells; and
correlating the corrected copy number to the 5-fluorouracil-based anticancer agent based on statistical analysis of the sensitivity of the cancer cells to the 5-fluorouracil-based anticancer agent, wherein the sensitivity is determined to be high for the resultant copy number of 2 or less and to be low for the resultant copy number of more than 2,
wherein the reagent is oligonucleotide primers for amplifying the whole or a part of dihydropyrimidine dehydrogenase gene which the length is about 17 to 25 bases, the primers are configured so that their 3' end sequences are not complementary to one another to prevent dimerization and so that they do not contain auto-complementary sequences of 4 or more bases to avoid formation of secondary structures within the primers, and
wherein a pair of the oligonucleotide primers is represented by SEQ ID NO: 5 and SEQ ID NO: 6.

5. A method of predicting the sensitivity of a cancer cell to a 5-fluorouracil-based anticancer agent, comprising:
providing a reagent for hybridizing to a region of dihydropyrimidine dehydrogenase gene present in cancer cells but not found in other genomic DNA;
reacting the reagent with dihydropyrimidine dehydrogenase gene in cancer cells derived from a subject;
generating data based on the reaction with dihydropyrimidine dehydrogenase for determining the copy number of dihydropyrimidine dehydrogenase gene as an indicator of subject's sensitivity to the 5-fluorouracil-based anticancer agent;
correcting the copy number using data obtained from a reference sequence that varies little in copy number between cancer cells and normal cells; and
correlating the corrected copy number to the 5-fluorouracil-based anticancer agent based on statistical analysis of the sensitivity of the cancer cells to the 5-fluorouracil-based anticancer agent, wherein the sensitivity is determined to be high for the resultant copy number of 2 or less and to be low for the resultant copy number of more than 2,
wherein the reference sequence is represented by a pair of forward primer and reverse primer, SEQ ID NO: 7 and SEQ ID NO: 8, respectively.

* * * * *

UNITED STATES PATENT AND TRADEMARK OFFICE
CERTIFICATE OF CORRECTION

PATENT NO.       : 8,440,398 B2
APPLICATION NO. : 12/161957
DATED            : May 14, 2013
INVENTOR(S)      : Kobunai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Eighth Day of September, 2015

Michelle K. Lee
*Director of the United States Patent and Trademark Office*